(12) United States Patent
Fisher et al.

(10) Patent No.: US 8,435,246 B2
(45) Date of Patent: May 7, 2013

(54) KNEE ARTHROPLASTY APPARATUS AND METHOD

(75) Inventors: Michael G. Fisher, Folsom, CA (US); Anthony K. Hedley, Paradise Valley, CA (US); Russell T. Nevins, Las Vegas, NV (US); Kevin M. Cordes, Rancho Cordova, CA (US)

(73) Assignee: Synvasive Technology, Inc., El Dorado Hills, CA (US)

( * ) Notice: Subject to any disclaimer, the term of this patent is extended or adjusted under 35 U.S.C. 154(b) by 434 days.

(21) Appl. No.: 12/616,747

(22) Filed: Nov. 11, 2009

(65) Prior Publication Data
US 2011/0106091 A1 May 5, 2011

Related U.S. Application Data

(63) Continuation of application No. PCT/US2009/063015, filed on Nov. 2, 2009.

(51) Int. Cl.
*A61B 17/56* (2006.01)

(52) U.S. Cl.
USPC ............................................. 606/88; 606/87

(58) Field of Classification Search ........... 606/88
See application file for complete search history.

(56) References Cited

U.S. PATENT DOCUMENTS

| | | | |
|---|---|---|---|
| 4,567,886 A | 2/1986 | Petersen | 128/92 |
| 4,952,213 A * | 8/1990 | Bowman et al. | 606/79 |
| 5,116,344 A | 5/1992 | Sundqvist | |
| 5,437,676 A | 8/1995 | Bouraly et al. | 606/88 |
| 5,624,444 A | 4/1997 | Wixon et al. | 606/88 |
| 5,681,316 A * | 10/1997 | DeOrio et al. | 606/88 |
| 5,916,220 A | 6/1999 | Masini | 606/88 |
| 6,063,091 A * | 5/2000 | Lombardo et al. | 606/88 |
| 6,090,114 A * | 7/2000 | Matsuno et al. | 606/88 |
| 7,104,996 B2 * | 9/2006 | Bonutti | 606/86 R |
| 7,442,196 B2 | 10/2008 | Fisher et al. | 606/88 |
| 7,578,821 B2 | 8/2009 | Fisher et al. | 606/88 |
| 2002/0133161 A1 | 9/2002 | Axelson, Jr. et al. | 606/88 |
| 2003/0153978 A1 | 8/2003 | Whiteside | |
| 2004/0039396 A1 | 2/2004 | Couture et al. | 606/87 |
| 2004/0172044 A1 | 9/2004 | Grimm et al. | 600/429 |
| 2005/0021039 A1 * | 1/2005 | Cusick et al. | 606/88 |

(Continued)

FOREIGN PATENT DOCUMENTS

| | | |
|---|---|---|
| CA | 2870063 A1 | 5/2011 |
| WO | WO-2008073999 A2 | 6/2008 |

OTHER PUBLICATIONS

PCT International Search Report and Written Opinion mailed on Jul. 27, 2010.

(Continued)

*Primary Examiner* — Kevin T Truong
*Assistant Examiner* — Zade Coley
(74) *Attorney, Agent, or Firm* — Schwegman, Lundberg & Woessner, P.A.

(57) ABSTRACT

A method for positioning a bone cutting guide on a tibia may involve coupling a cutting guide positioning apparatus with a tibia, adjusting the positioning apparatus in a varus/valgus orientation, adjusting the positioning apparatus in an anterior/posterior orientation, adjusting the positioning apparatus up or down to select a tibial bone resection level, and contacting a cutting guide with the tibia, using the adjusted positioning apparatus.

13 Claims, 18 Drawing Sheets

U.S. PATENT DOCUMENTS

| | | | |
|---|---|---|---|
| 2005/0070897 A1* | 3/2005 | Petersen | 606/53 |
| 2005/0113846 A1 | 5/2005 | Carson | |
| 2005/0143746 A1 | 6/2005 | Steffensmeier et al. | |
| 2005/0222573 A1 | 10/2005 | Branch et al. | |
| 2006/0241639 A1 | 10/2006 | Kuczynski et al. | 606/86 |
| 2007/0043375 A1 | 2/2007 | Anissian | |
| 2007/0219559 A1* | 9/2007 | Heavener et al. | 606/87 |
| 2008/0065085 A1 | 3/2008 | Couture et al. | 606/87 |
| 2008/0195109 A1 | 8/2008 | Hunter et al. | 606/87 |
| 2009/0043310 A1* | 2/2009 | Rasmussen | 606/88 |
| 2009/0234360 A1* | 9/2009 | Alexander | 606/88 |

OTHER PUBLICATIONS

PCT International Search Report and Written Opinion mailed on Jan. 10, 2011 issued in PCT Application No. PCT/US2010/028729.

U.S. Appl. No. 12/729,222, filed Mar. 22, 2010, Bone Positioning Device and Method.

"U.S. Appl. No. 12/729,222, Final Office Action mailed Nov. 15, 2012", 12 pgs.

"U.S. Appl. No. 12/729,222, Non Final Office Action mailed Jul. 13, 2012", 10 pgs.

"U.S. Appl. No. 12/729,222, Response filed Jun. 4, 2012 to Restriction Requirement mailed May 3, 2012", 2 pgs.

"U.S. Appl. No. 12/729,222, Response filed Oct. 12, 2012 to Non Final Office Action mailed Jul. 13, 2012", 8 pgs.

"U.S. Appl. No. 12/729,222, Restriction Requirement mailed May 3, 2012", 6 pgs.

"International Application Serial. No. PCT/US2009/063015, International Preliminary Report on Patentability mailed May 8, 2012", 6 pgs.

"International Application Serial No. PCT/US2009/063015, International Search Report mailed Jul. 27, 2010", 4 pgs.

"International Application Serial No. PCT/US2009/063015, Written Opinion mailed Jul. 27, 2010", 5 pgs.

* cited by examiner

KNEE ARTHROPLASTY APPARATUS AND METHOD

CROSS-REFERENCE TO RELATED APPLICATIONS

This application is a Continuation of PCT International Application No. PCT/US2009/063015 filed on Nov. 2, 2009, the disclosure of which is incorporated herein in its entirety.

BACKGROUND

Embodiments of the present technology relate to medical/surgical devices, systems and methods. More specifically, embodiments of the present technology relate to devices, systems and methods for enhancing a knee surgery procedure.

Approximately 550,000 total knee replacement surgeries (also referred to as total knee arthroplasty ("TKA") are performed annually in the U.S. for the treatment of chronic knee pain and dysfunction. As the U.S. and world populations become older and more obese, knee replacement surgery will become even more common, as knee joints endure greater and greater wear and tear from their increased loads and years of stress. Conventional TKA surgery is often very effective but also very invasive and sometimes imprecise, thus leading to less than ideal outcomes.

The knee is generally defined as the point of articulation of the femur with the tibia. Structures that make up the knee include the distal femur, the proximal tibia, the patella, and the soft tissues within and surrounding the knee joint. Four ligaments are especially important in the functioning of the knee—the anterior cruciate ligament, the posterior cruciate ligament, the medial collateral ligament, and the lateral collateral ligament. In an arthritic knee, protective cartilage at the point of articulation of the femur with the tibia has been worn away to allow the femur to directly contact the tibia. This bone-on-bone contact causes significant pain and discomfort. The primary goals of a TKA procedure are to replace the distal end of the femur, the proximal end of the tibia, and often the inner surface of the patella with prosthetic parts to avoid bone-on-bone contact and provide smooth, well-aligned surfaces for joint movement, while also creating a stable knee joint that moves through a wide range of motion.

In a TKA surgery, the surgeon cuts open the knee, flips the patella bone out of the way, cuts bone from the distal end of the femur and from the proximal end of the tibia, and installs new, manmade, prosthetic ends onto the femur and tibia to form a new knee joint. In some TKA procedures, the interior surface of the patella may also be covered with a prosthetic. Cutting open the knee, moving the patella, sawing off bone segments, and implanting the manmade implants is a very invasive, though effective, procedure. Determining how to cut the ends of the femur and tibia to ensure proper alignment and balancing of ligament tension in the new, prosthetic knee joint can be very challenging and often involves more art than science. An artificial knee joint in which the ligament tension is not well balanced endures significantly more wear and tear than one that is properly balanced, and yet, this proper balance is very difficult to achieve. As a consequence, TKA surgery performed on younger patients typically needs to be redone one or more times during the patient's life.

Due to the invasiveness and imprecision of traditional TKA, there is a need for improved techniques and devices in this field. A number of minimally invasive (or "less invasive") TKA techniques, involving smaller incision sizes and reduced trauma to the patient have been developed in an effort to reduce patient recovery time. Some of these minimally invasive techniques, as well as other innovations, have also sought to enhance and/or facilitate TKA by making it more precise and repeatable and thus, ideally, reducing wear and tear on artificial knees and the need for repeat procedures. Improved techniques and devices would also mean enhanced outcomes for all TKA patients, with better functioning of the knee joint and longer useful life of the artificial knee.

One of the greatest challenges in TKA surgery is to properly balance ligament tension, especially in the medial and lateral collateral ligaments, through a full range of motion of the knee. The collateral ligaments, which connect the distal femur and proximal tibia on the medial and lateral aspects of the knee, account for much of the stability and movement of the knee. If one of the collateral ligaments is too lax or too tight relative to the other collateral ligament, the knee will typically be unstable, range of motion may be limited, the patella may move (or "track") improperly, and the femur and/or tibia may wear unevenly, leading to arthritis and pain. Uneven ligament tension after TKA surgery will typically cause joint instability and poor patellar tracking, limited range of motion, and impaired function of the knee, as well as uneven, increased wear of the prosthetic device, which often necessitates repeat surgery. Thus, it is imperative for the short- and long-term success of a TKA procedure to achieve balanced ligament tension in the knee through a full range of motion.

Balancing ligament tension during TKA surgery is complicated by the fact that the natural knee does not operate like a hinge moving about a single axis. The knee exhibits dynamic external rotation of the tibia relative to the femur as the knee moves from its flexed to its fully extended position. This automatic rotation of the tibia occurs in the opposite direction when the knee is flexed from its fully extended position to produce an internal rotation of the tibia relative to the femur. Thus, the natural knee exhibits a rotary laxity that allows the tibia to rotate through a limited internal and external arc during knee flexion. In addition, the femur translates anteriorly and posteriorly as the tibia is being flexed about it, bringing yet another movement variable into the equation. Thus, the ligaments of the knee, along with the femur, tibia and patella, create a truly dynamic bio-mechanism, making ligament tension balancing in TKA surgery extremely challenging. This challenge is even greater in minimally invasive TKA procedures, in which incisions are smaller than those made in "open" TKA surgeries. Additionally, the incision made during minimally invasive TKA surgery is biased to the medial side, leaving the lateral side of specifically the distal femur "closed" to access of front or end loaded surgical instruments One way surgeons try to balance ligament tension during TKA procedures is by cutting one or more ligaments to release tension from one part of the joint ("ligament release"). The disadvantage of ligament release, however, is that once a ligament is cut it cannot be regenerated, and the ligaments of the knee provide much needed stability to the knee joint.

Rather than or in addition to ligament release, the components of a total knee prosthesis may be selected and positioned to balance ligament tension. Since the femoral and tibial components of the knee prosthesis are attached to cut surfaces of the distal femur and proximal tibia respectively, placement and orientation of the femoral and tibial bone cuts are very important for balancing knee ligament tension. As with ligament release however, it is often very challenging to position the femoral and tibial bone cuts and prosthetic components to provide ideal ligament tension through the range of motion. This is due primarily to the complexity of motion about the knee, as described above, and the difficulty of assessing and making the bone cuts during the procedure to achieve desired ligament tension through the full range of motion.

Improved methods and apparatus for facilitating and/or enhancing femoral bone cuts have been described by the assignee of the present application in, for example, U.S. Pat. Nos. 7,578,821 and 7,442,196. Few if any innovations have been made, however, to facilitate or enhance tibial bone cuts in a TKA procedure.

To make a tibial cut in a typical TKA procedure, an orthopedic surgeon typically uses a cutting block or cutting guide temporarily attached to the front of the tibia via a rod that is typically attached to an ankle clamp at the distal end to the tibia (an extramedulary rod) and aligned approximately with the mechanical axis of the anterior surface of the tibia. The cutting block is used to guide a surgical saw blade or rotary tool in making the tibial bone cut. Positioning such a cutting block, therefore, is crucial to forming well-positioned bone cuts for attachment of the tibial and femoral prosthetic components. The tibial cut is the foundation of a TKA, as it affects the spacing, alignment and balance between the tibia and femur when the knee is in flexion (the flexion gap) the spacing, alignment and balance between the tibia and femur when the knee is in extension (the extension gap) and all points of articulation between extension and flexion. Typically, the tibial component of a knee prosthesis is positioned on a flat, horizontal cut surface of the proximal tibia (at a 90 degree "varus/valgus" angle relative to the long axis of the tibia), and the position and orientation of the tibial component typically do not vary greatly from knee to knee. However, by making a cut on the tibia at 90 degrees to the long axis of the bone, a bigger space is created laterally than medially, due to the tibia's natural approximately 3 degrees of varus slope. Furthermore, the "classic" 90-degree tibial bone cut is typically made by the surgeon simply approximating the 90-degree angle. Therefore, the usual cut made to the tibia in TKA is not necessarily ideal and is made by approximation. Thus, improvements to the angle and precision of the tibial cut may improve the ligament balancing and overall result of a TKA procedure.

Therefore, a need exists for improved devices, systems and methods for enhancing TKA surgery and specifically for enhancing and/or facilitating the positioning of one or more tibial bone cuts made during a TKA procedure to accommodate a tibial prosthetic. Ideally, such devices, systems and methods would allow a physician to effectively select an angle at which to make a tibial bone cut and would help the physician more accurately make the cut at the selected angle. Such devices, systems and methods would also ideally be simple to use in conjunction with cutting guides, saw blades or burs, robotic and navigational systems, and/or any other equipment used by a surgeon in a TKA procedure. At least some of these objectives will be met by various embodiments of present technology.

BRIEF SUMMARY

The present technology provides devices, systems and methods for positioning a bone cut on a tibia as part of a TKA or other knee surgery procedure. These devices, systems and methods generally help a physician achieve balancing of ligaments during the knee surgery procedure, thus potentially enhancing the outcome of the procedure and/or reducing wear and tear of an artificial knee joint implanted during the procedure.

In one aspect, a method for positioning a bone cutting guide on a tibia may involve coupling a cutting guide positioning apparatus with a tibia, adjusting the positioning apparatus in a varus/valgus orientation, adjusting the positioning apparatus in an anterior/posterior orientation, adjusting the positioning apparatus up or down to select a tibial bone resection level, and contacting a cutting guide with the tibia, using the adjusted positioning apparatus. In some embodiments, the method may further include emitting light in a linear configuration from the cutting guide positioning device. In such embodiments, adjusting the apparatus in the varus/valgus orientation may involve moving the light to shine along approximately a midline of an anterior surface of the tibia, and adjusting the apparatus in the anterior/posterior orientation may involve moving the light to shine along approximately a midline of a side of the tibia. In one embodiment, the side of the tibia along which light is shone is the medial side. Optionally, this method may further involve swinging a swing arm of the cutting guide positioning apparatus approximately 90 degrees between the steps of adjusting in the varus/valgus orientation and adjusting in the anterior/posterior orientation. One embodiment further involves locking in the varus/valgus orientation before swinging the swing arm.

In some embodiments, the cutting guide is removably coupled with the guide positioning apparatus during the adjusting steps. In some embodiments, the method further includes attaching the cutting guide to the tibia. Optionally, the method may further include removing the positioning apparatus from the tibia and the cutting guide and making at least one cut on the tibia guided by the cutting guide.

In one embodiment, adjusting the positioning apparatus up or down to select a tibial bone resection level involves moving a resection level adjustment member up or down to contact a stylus touching an upper surface of the tibia and extending to a location anterior to and below the upper surface. In the present application, the "upper surface" of the tibia means the superior articular surface (or surfaces) of the tibia before any tibial bone cuts have been made. These superior surfaces are often referred to as the medial and lateral articular surfaces or the medial and lateral facets of the tibia. For the purposes of this application, any of the terms "upper surface," "articular surface," "facet" or "extreme proximal end" of the tibia may be used interchangeably. In one embodiment, the location anterior to and below the upper surface is between about 8 mm and about 11 mm below the upper surface, and the upper surface is the lateral articular surface of the tibia.

In some embodiments, coupling the cutting guide positioning apparatus with the tibia involves advancing the at least one hole in the apparatus over at least one reference pin attached to the tibia. In one embodiment, two foot pads of the positioning device are advanced over two reference pins to contact the medial and lateral articular surfaces of the tibia.

In another aspect, a method for positioning a bone cutting guide on a tibia may include: coupling a cutting guide positioning apparatus with a tibia, wherein the positioning apparatus is coupled with a tibial cutting guide; emitting a light from the positioning apparatus; adjusting the positioning apparatus in a varus/valgus orientation to shine the light approximately along a midline of an anterior surface of the tibia; swinging a swing arm of the positioning apparatus approximately 90 degrees to shine the light along a side of the tibia; adjusting the positioning apparatus in an anterior/posterior orientation to shine the light approximately along a midline of the side of the tibia; adjusting the positioning apparatus up or down to select a tibial bone resection level; and attaching the tibial cutting guide to the tibia, using the adjusted positioning apparatus.

In another aspect, a device for positioning a bone cut on a tibia may include: a tibial attachment member; a coupler moveably attached to the tibial attachment member; a rotationally moveable arm rotationally attached to the coupler; a swing arm coupled with the rotationally moveable arm via an axle such that a free end of the swing arm swings from an anterior position to a side position; a light emitting member coupled with the swing arm at or near the free end for emitting light along the tibia; a varus/valgus adjustment member for adjusting the rotationally moveable arm to direct the emitted light approximately along a midline of an anterior surface of the tibia; an anterior/posterior adjustment member for adjusting the coupler in an anterior/posterior orientation relative to the tibial attachment member to direct the emitted light approximately along a midline of a side of the tibia; and a tibial bone resection level adjustment member for selecting a level for resecting the tibia.

In some embodiments, the tibial attachment member may include at least one foot pad for contacting an articular surface of an uncut tibia and at least one hole for passing the attachment member over a reference pin attached to the tibia. In one embodiment, the attachment member includes a medial articular surface footpad having a first hole and a lateral articular surface footpad having a second hole.

In some embodiments, the light emitting member emits light in a linear or planar configuration. The side of the tibia is the medial side in some embodiments, and the swing arm rotates between a first position in which the light shines along the anterior surface of the tibia and a second position in which the light shines along the medial side of the tibia. Alternatively, the lateral side of the tibia may be addressed in other embodiments. Some embodiments may further include a stylus coupled with the tibial attachment member and configured to extend from an upper surface of the tibia to a location anterior to and below the upper surface. This tibial bone resection level adjustment member is adjustable to contact the tibial cutting guide with the stylus at the location. In some embodiments, the device further includes a tibial cutting guide holder, where adjustments of the adjustment members adjust a position of the cutting guide holder.

In another aspect, a system for positioning a tibial cutting guide on a tibia may include a tibial cutting guide and a cutting guide positioning device. The positioning device may include: a tibial attachment member; a coupler moveably attached to the tibial attachment member; a rotationally moveable arm rotationally attached to the coupler; a swing arm coupled with the rotationally moveable arm via an axle such that a free end of the swing arm swings from an anterior position to a side position; a light emitting member coupled with the swing arm at or near the free end for emitting light along the tibia; a varus/valgus adjustment member for adjusting the rotationally moveable arm to direct the emitted light approximately along a midline of an anterior surface of the tibia; an anterior/posterior adjustment member for adjusting the coupler in an anterior/posterior orientation relative to the tibial attachment member to direct the emitted light approximately along a midline of a side of the tibia; a tibial bone resection level adjustment member for selecting a level for resecting the tibia; and a tibial cutting guide holder, where adjustments of the adjustment members adjust a position of the cutting guide holder.

Embodiments of the present invention comprise means for implementing the methods of the enclosed claims, and in particular, method claims 15-29.

Generally, the tibial cutting guide holder is moveable relative to the rotationally moveable arm to move the tibial cutting guide into contact with the tibia. In some embodiments, the system may further include at least one reference pin for removably attaching the tibial attachment member of the guide positioning device to the tibia. Optionally, the system may further include at least one cutting guide fastener, such as a pin or rod, for attaching the tibial cutting guide to the tibia.

For a further understanding of the nature and advantages of the technology, reference should be made to the following description taken in conjunction with the accompanying figures. However, each of the figures is provided for the purpose of illustration and description only and is not intended to limit the scope of the embodiments of the present technology.

DETAILED DESCRIPTION

The devices, systems and methods described below may be used in various embodiments to enhance and/or facilitate a total knee arthroplasty (TKA) procedure, a partial knee arthroplasty procedure, or any other suitable knee surgery procedure in which one or more cuts are made on a tibia, typically a proximal end of a tibia. Generally, the embodiments described herein provide a means for positioning a bone cut on a tibia. Although the following description may frequently refer to TKA procedures, the described embodiments may also be used for partial knee arthroplasty procedures or other knee procedures in which tibial bone cuts are made.

Figure 1A:
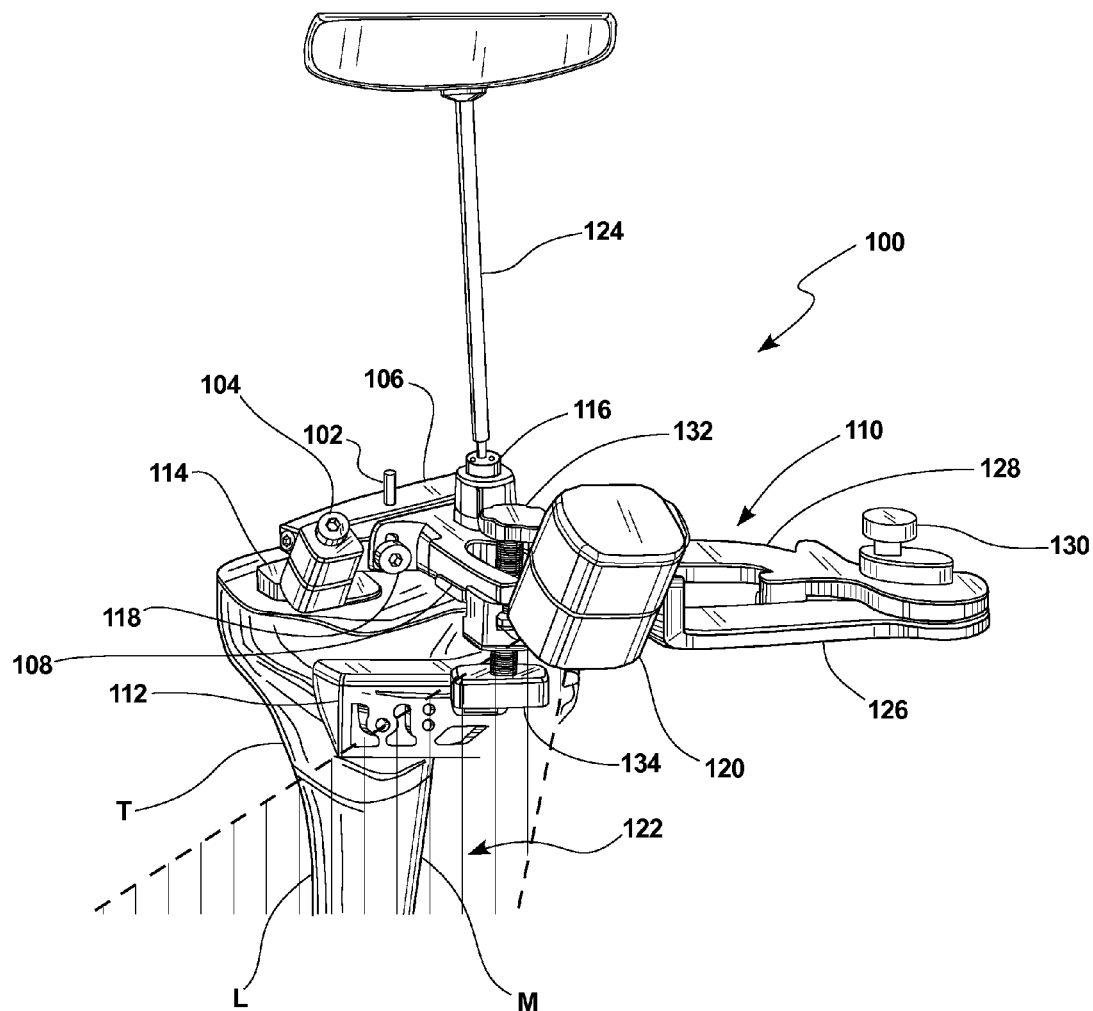
FIG. 1A is a perspective view of a bone cut positioning system coupled with a proximal end of a tibia, according to one embodiment.

Referring to FIG. 1A, one embodiment of a bone cut positioning system 100 is shown attached to a tibia T. In this view, the tibia T is of a right leg and is in an anterior (front) facing orientation, with the lateral side L of the tibia T toward the left side of the figure and the medial side M of the tibia toward the right side of the figure.

Figure 1B:
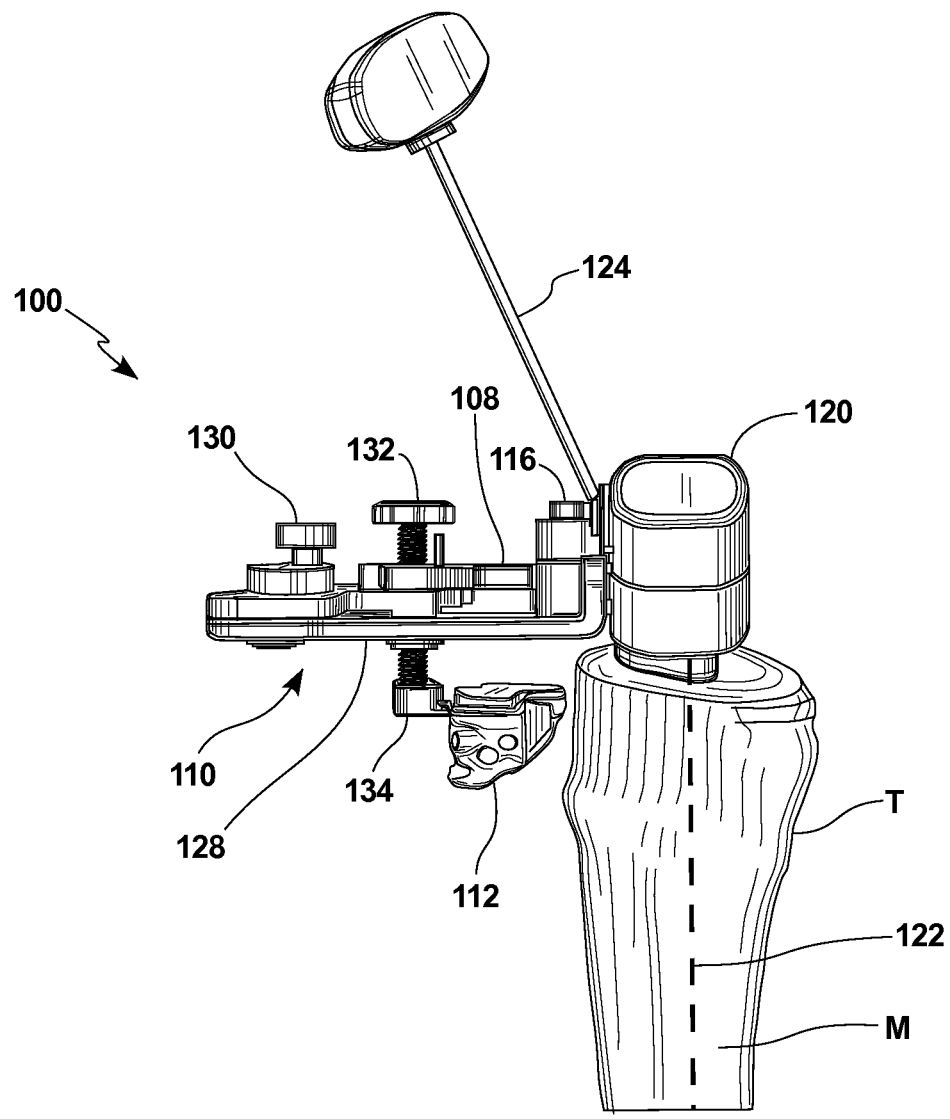
FIG. 1B is a side view of the system and tibia of FIG. 1A.
Figure 1C:
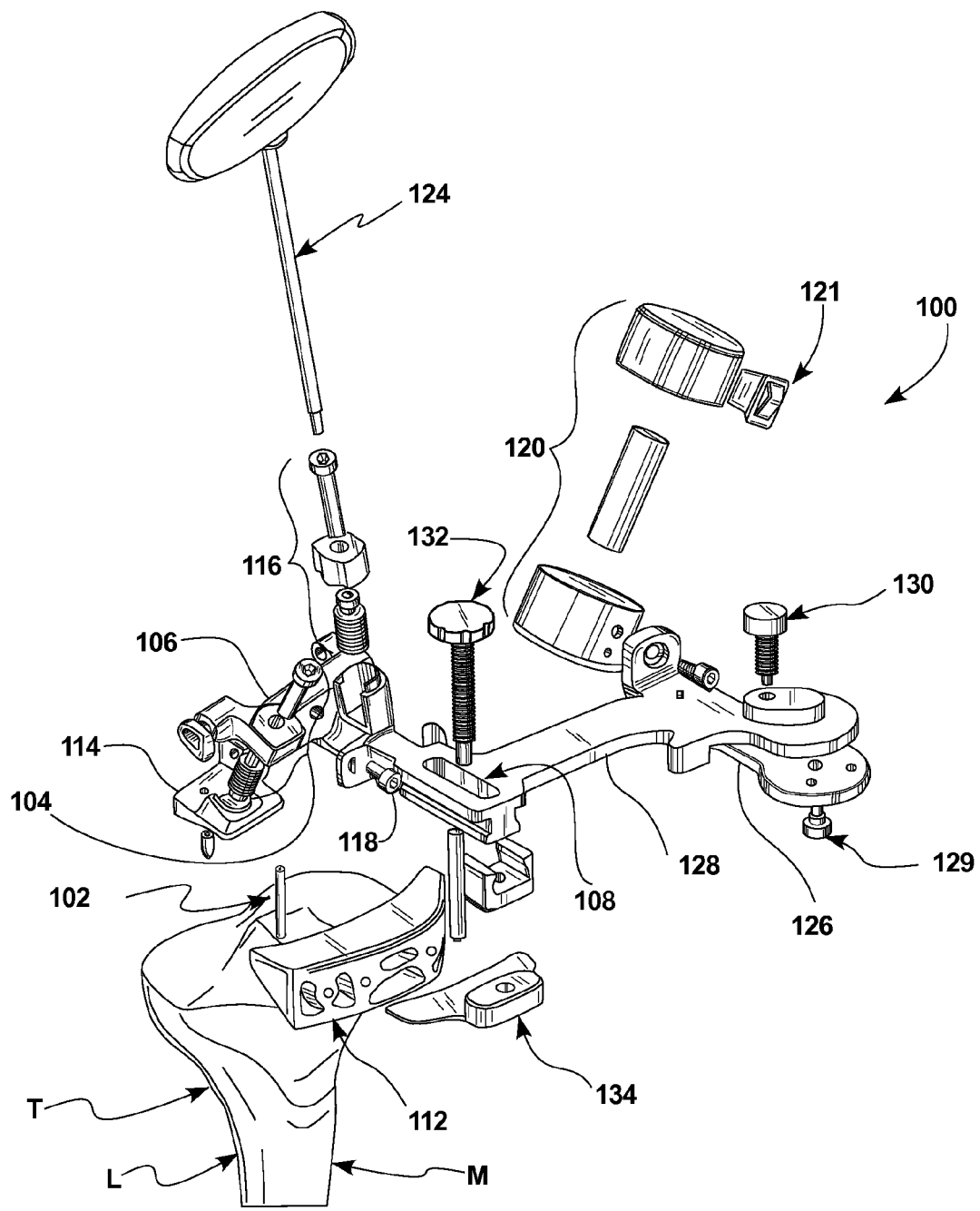
FIG. 1C is an exploded perspective view of the system of FIGS. 1A and 1B.

FIG. 1B shows system 100 in place with the medial side M of the tibia T facing out of the page and the system 100 rotated to address the medial side M, as will be explained in more detail below. FIG. 1C shows an exploded view of system, and FIG. 1D shows an exploded view of part of system 100.

In the embodiment of FIGS. 1A-1D, system 100 for enhancing and/or facilitating positioning a bone cut on a tibia T includes a bone cutting guide 112 (or "guide block") and a bone cut positioning device 110. In alternative embodiments, positioning device 110 may be adapted to position a bone cut without using cutting guide 112, or by using a different variation of cutting guide 112. In various embodiments, bone cutting guide 112 may be any currently available or subsequently developed bone cutting guide 112. Because bone cutting guides or guide blocks are well known in the art, they will not be described further herein. In various embodiments, bone cutting guide 112 may be provided as part of the system 100 or alternatively may be available separately.

In some embodiments, bone cut positioning device 110 may be coupled to the tibia T via a tibial reference pin 102 (or "tibial pin") inserted into the tibia T. Pin 102 may be part of system 100 or may be available separately, in various embodiments. Pin 102 may be used in place of extramedulary rods.

Figure 1D:
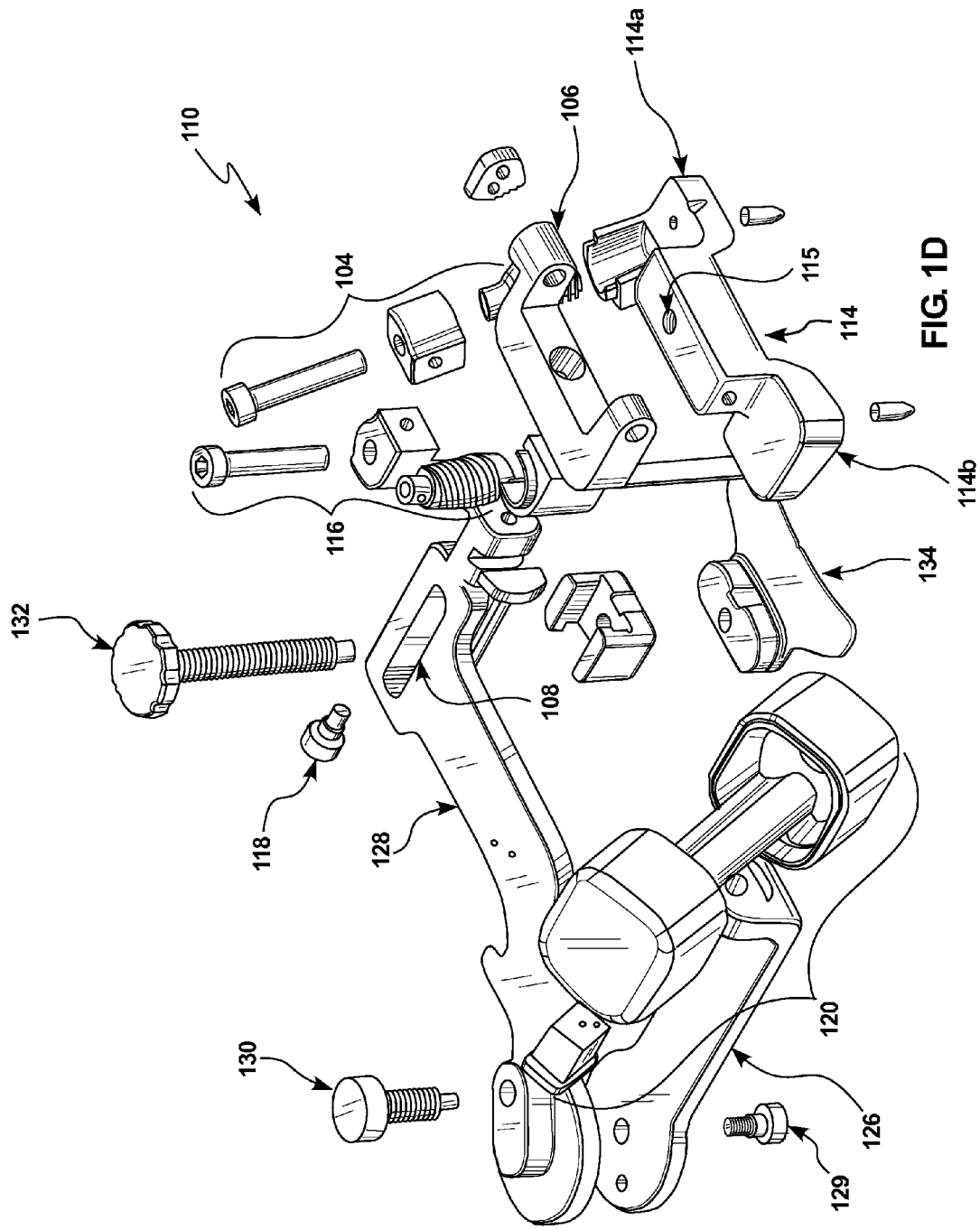
FIG. 1D is an exploded view of a portion of the system of FIGS. 1A-1C.

In the embodiment of FIGS. 1A-1D, bone cut positioning device 110 includes a number of component parts, some of which may be more easily viewed in FIGS. 1C and 1D. As shown in FIG. 1D, for example, positioning device 110 may include a tibial attachment member 114 that attaches directly to the tibia T via a hole 115 for accepting pin 102 and is rotationally moveable relative to the tibia T during use of positioning device 110. In this embodiment, tibial attachment member 114 includes two foot pads—a right foot pad 114a and a left footpad 114b—for contacting the proximal end of the tibia T. In alternative embodiments, one foot pad or more than two foot pads may be used. Positioning device 110 also includes a coupler 106, which attaches a rotationally moveable arm 128 to tibial attachment member 114. A varus/valgus adjustment member 116 and an anterior/posterior adjustment member 104 (or "tibial slope adjustment member") move members 128 and 106 relative to the tibial attachment member 114 to adjust the orientations of device 110 and thus adjust the orientation of cutting guide 112 relative to the tibia T. In the embodiment shown, adjustment members 116, 104 are threaded, bolt-like apparatus that are adjustable by an adjustment device 124, such as but not limited to the Allen wrench shown in the figure. In alternative embodiments, any other suitable adjustment apparatus may be used for adjusting coupler 106 relative to tibial attachment member 114, such as rack and pinion gears, ring and pinion gears or the like.

Rotationally moveable arm 128 may be rotated during a positioning process by adjusting adjustment member 116, though rotationally moveable arm 128 remains anterior to the tibia T during the positioning procedure. Rotationally moveable arm 128 includes a slot 108 for receiving a tibial bone resection level adjustment member 132, which is coupled with a cutting guide attachment member 134, which in turn is removably coupled with cutting guide 112. In one embodiment, tibial bone resection level adjustment member 132 may comprise a bolt-like apparatus with threads and an adjustment knob, as pictured in FIGS. 1A-1D. Slot 108 is configured to allow resection level adjustment member 132 to slide horizontally back and forth to move cutting guide 112 toward and away from the tibia T and to move vertically up and down to select a height (i.e., bone resection level) at which cutting guide 112 will create a bone resection plane to be established by a saw blade upon the tibia T. In some embodiments, resection level adjustment member 132 may be locked or set at a desired level after adjustment.

Rotationally moveable arm 128 is coupled with a swing arm 126 (or "swivel arm") at a pivot point via an axle 129. Optionally, a lock screw 130 may be included to lock swing arm 126 relative to rotationally moveable arm 128, typically in either a 0° (facing anterior tibia) or a 90° (facing side tibia) orientation. Swing arm 126, in turn, is coupled with a light emitting apparatus 120, generally including a light source and in some embodiments an on/off switch 121. Light emitting apparatus 120 is capable of directing a plane of light 122 (FIGS. 1A and 1B) toward a surface of a tibia T for guiding orientation and adjustment of device 110. In alternative embodiments, the light emitted by light emitting apparatus may be in the form of a beam, fan, or any other suitable linear configuration for shining along a length of a tibia. In some embodiments, light emitting apparatus 120 may be tilted by a user to ensure that the plane of light 122 is directed along the tibial surface.

Swing arm 126 may be configured to rotate from the 0° position toward either side to the 90° position. In one embodiment, for example, swing arm 126 may be rotated from the 0° position to a 90° position facing a medial side of a tibia on a first knee of a patient and may be rotated in the opposite direction on the second knee of the patient so that the 90° position also faces the medial side of that second tibia. In alternative embodiments, the 90° position may be either a medial side or a lateral side of a tibia.

Coupler 106 may be adjusted in the anterior/posterior orientation via adjustments to an anterior/posterior adjustment member 104. In various embodiments, coupler 106 may be locked in the anterior/posterior orientation as well as or alternative to locking in the varus/valgus orientation. In some embodiments, adjustment members 116, 104 and locking member 118 may all be screws, bolts or other threaded adjustment members. In the embodiment shown, adjustment members 116, 104 and locking member 118 are adjusted using Allen wrench 124, although in alternative embodiments any suitable adjustment device may be used, such as a screw driver, wrench, fingers or the like.

Referring to FIGS. 1C and 1D, tibial bone resection adjustment member 132 passes through slot 108 and attaches to cutting guide attachment member 134. Cutting guide attachment member 134 is configured as a platform for holding cutting guide 112. In alternative embodiments, attachment member 134 may have any other suitable shape, size or configuration for removably coupling with one or various different cutting guides.

The various components of bone cut positioning device 110 may be manufactured from any suitable materials. For example, in some embodiments many of the components may be made of stainless steel or other metal, which other components may be plastic. In a typical embodiment, all materials of device 110 may be sterilizable by commonly used sterilization techniques, such as gamma irradiation, EtO sterilization and the like. Any adjustment screws, bolts, trunions or the like may be substituted with similar adjustment means in alternative embodiments, and adjustment devices such as Allen wrenches, screw drivers and the like may be likewise substituted.

Referring now to FIGS. 2A-2J, a method is shown for positioning a bone cut on a tibia as part of a TKA or other knee surgery procedure according to one embodiment. As shown in a perspective view in FIG. 2A, bone cut positioning system 100 (bone cut positioning device 110 and cutting guide 112) may first be coupled with the tibia T via reference pin 102. When initially attached, bone cut positioning device 110 may be adjusted such that swing arm 126 positions light emitting device 120 at the 0° angle, i.e., facing the anterior surface of the tibia T. Plane of light 122 may be generally directed toward the anterior surface of the tibia T but may not be initially aligned to shine directly along the midline of the anterior surface.

Figure 2A:
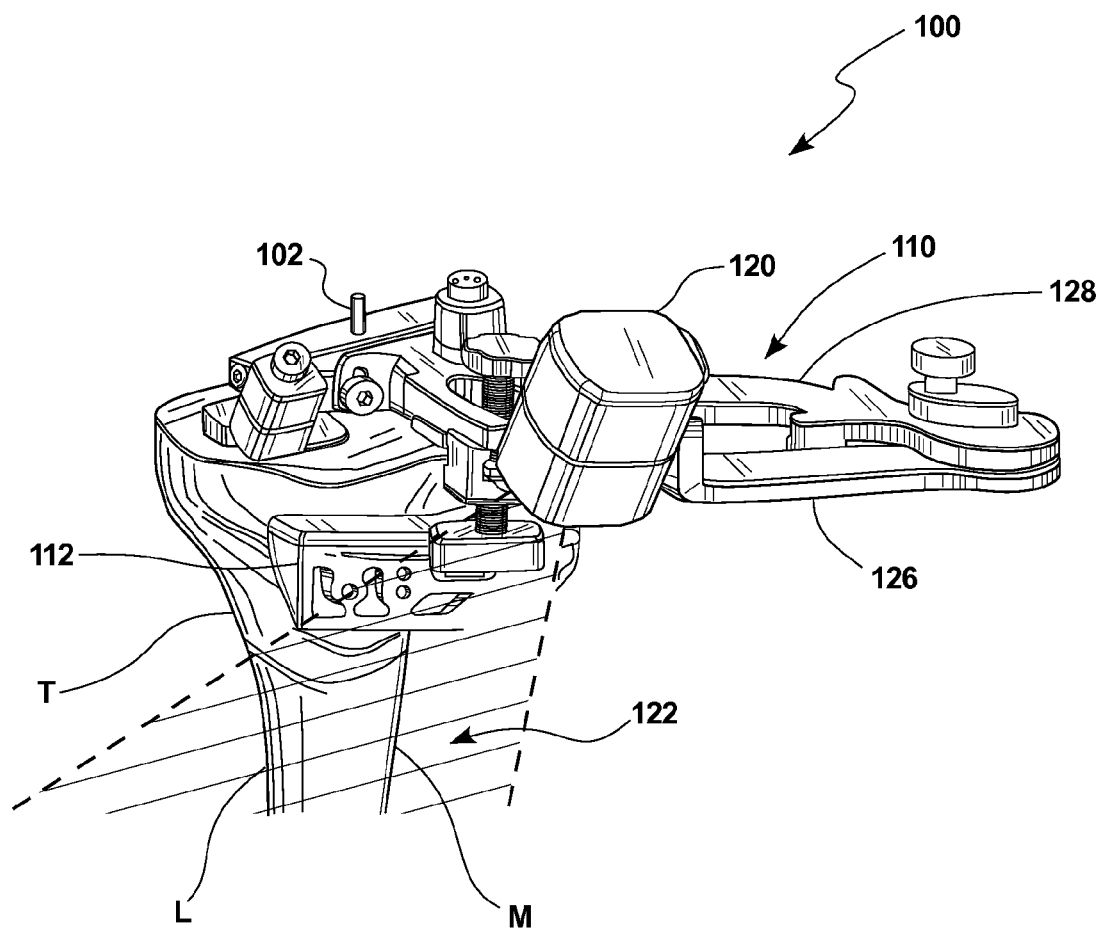
FIGS. 2A-2J illustrate a method for positioning a bone cut using a bone cut positioning system, according to one embodiment.
Figure 2B:
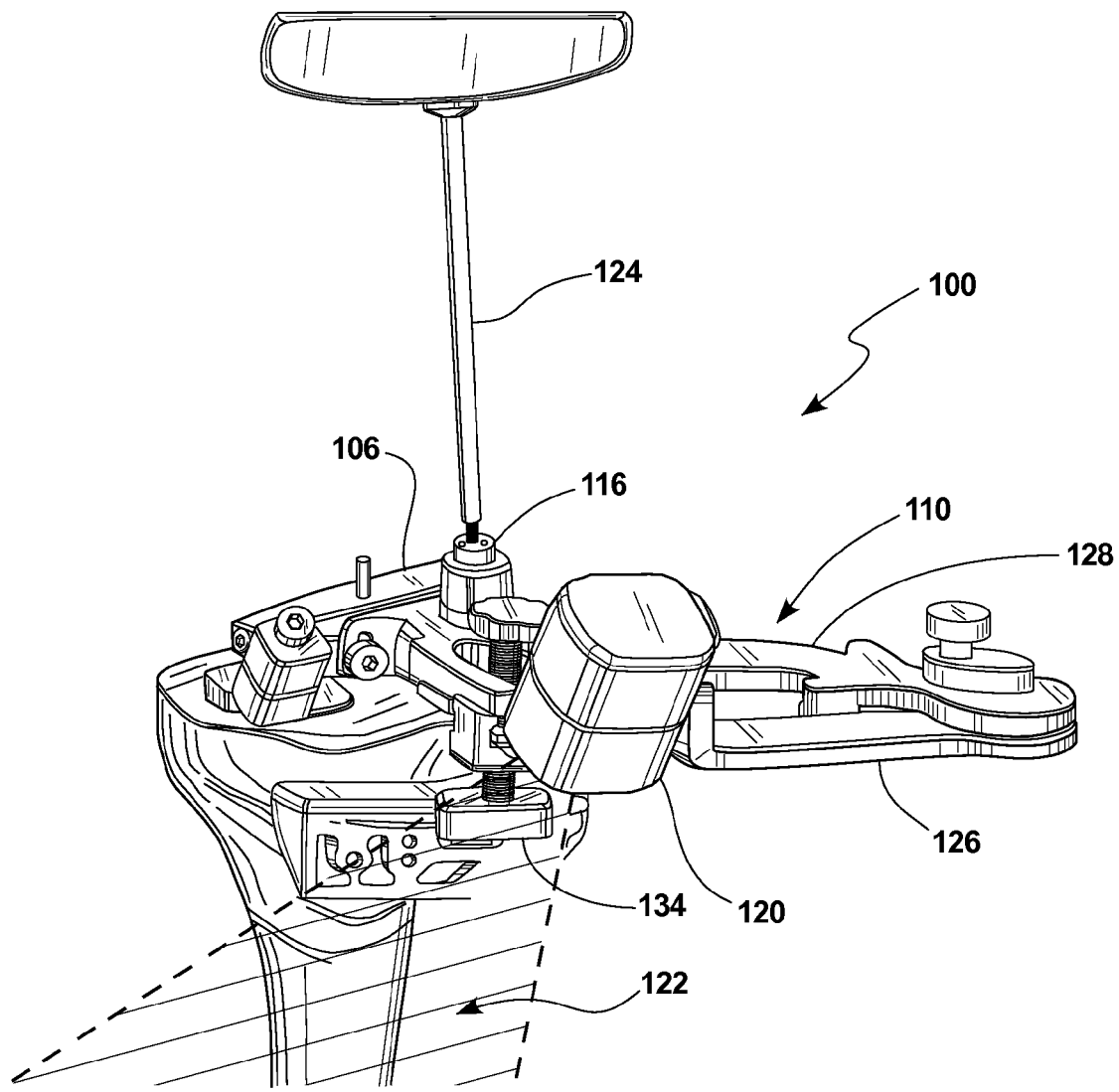
Figure 2C:
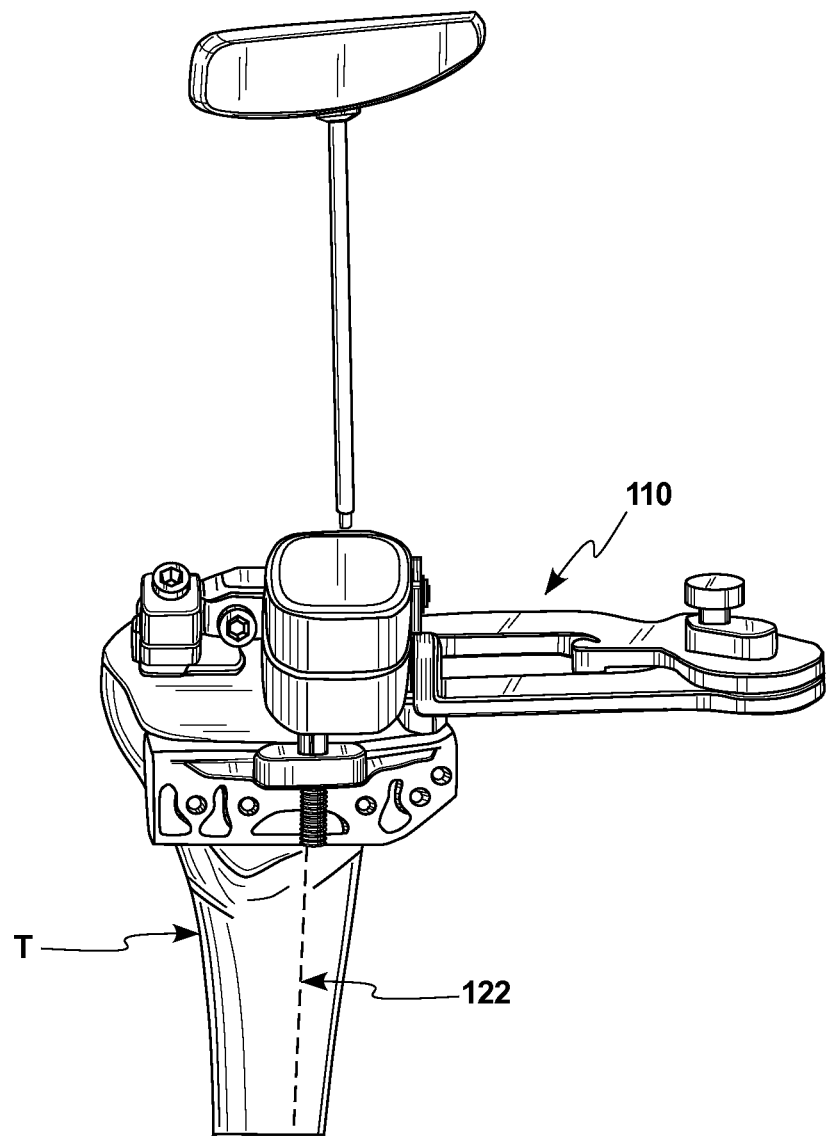

As shown in FIGS. 2B and 2C, adjustment device 124 may be used to adjust varus/valgus adjustment member 116, which in turn moves rotationally moveable arm 128, swing arm 126 and light emitting member 120 in the varus/valgus orientation. This movement adjusts the direction of plane of light 122 such that, as shown in FIG. 2C, light 122 may be directed approximately along a midline of the anterior surface of the tibia T. Positioning device 110 is configured such that when plane of light 122 is directed along approximately the midline of the anterior surface of the tibia T, as in FIG. 2C, cutting guide 112 is oriented in a desirable varus/valgus orientation for making a tibial bone cut.

Figure 2D:
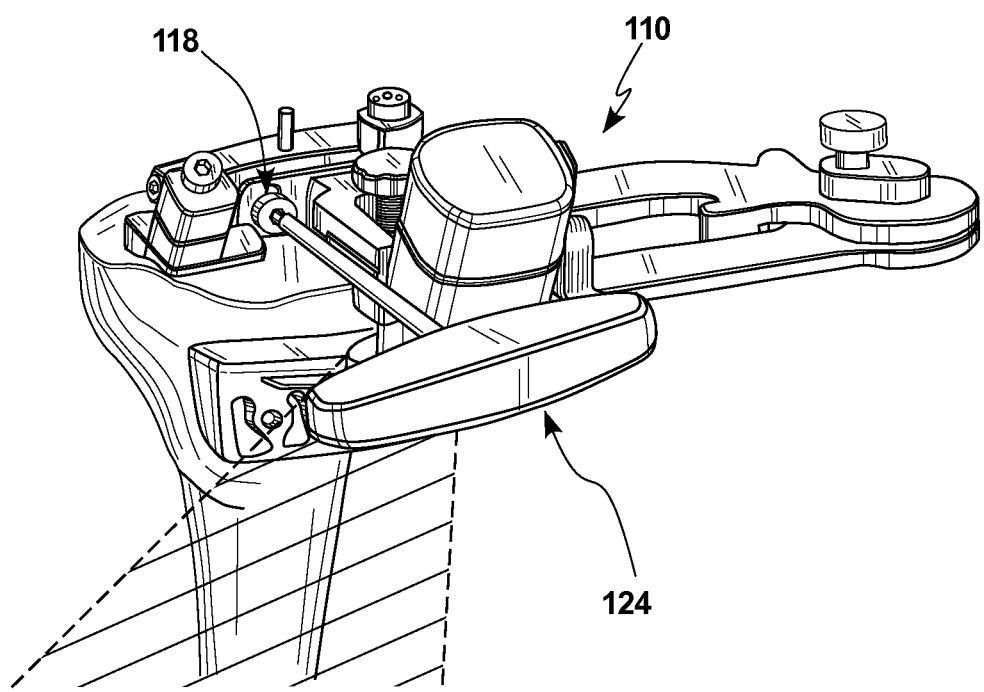

In one embodiment, and with reference now to FIG. 2D, adjustment device 124 may next be used to lock in the varus/valgus adjustment of positioning device 110 via locking member 118. In alternative embodiments, it may not be necessary to lock in the varus/valgus adjustment or the adjustment may be locked in automatically by an automatic locking mechanism of device 110.

Figure 2E:
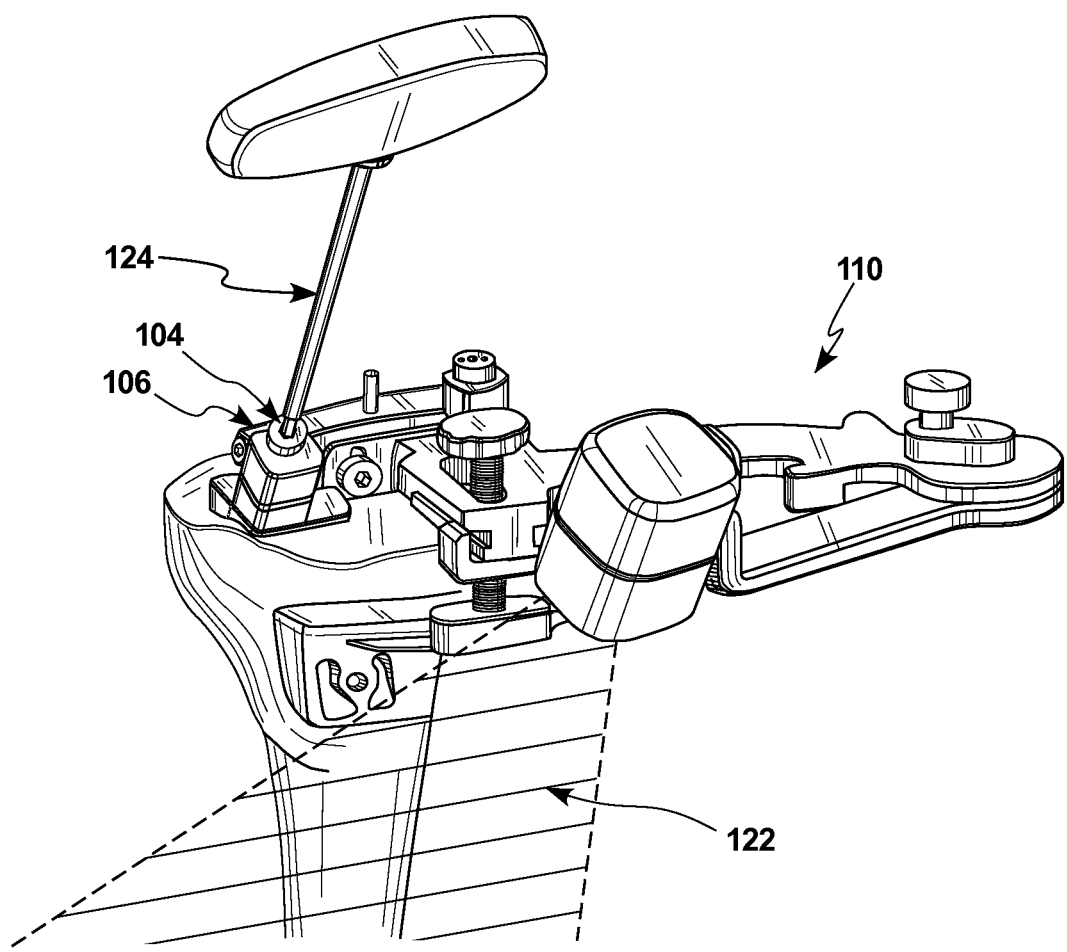
Figure 2F:
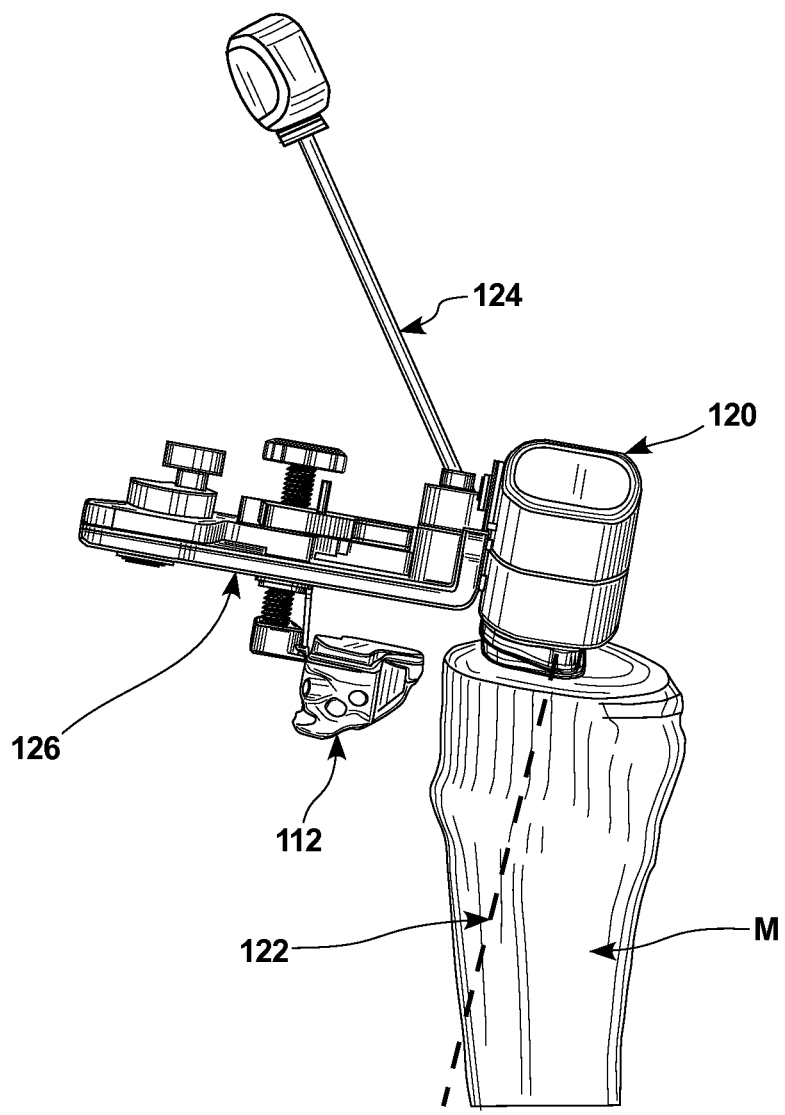

Referring to FIG. 2E, adjustment device 124 may next be coupled with anterior/posterior adjustment member 104. As shown in FIG. 2F, swing arm 126 may be rotated about axle 129 (now visible) approximately 90° to position light illuminating member 120 to direct plane of light 122 along the medial side M of the tibia T. Although in an alternative embodiment the lateral side L of the tibia T may be used for the bone cut positioning method, the medial side M is generally the preferred side for orienting and positioning device 110 and cutting guide 112.

Figure 2G:
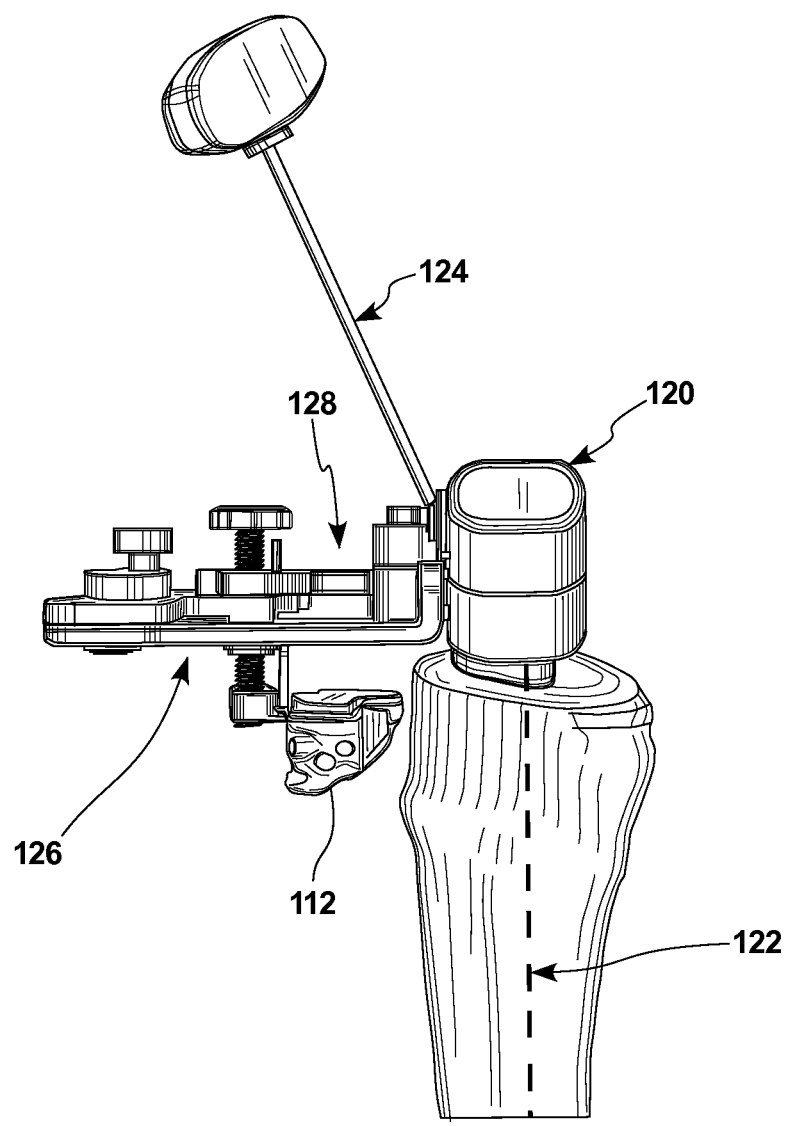

As shown in FIG. 2G, adjustment device 124 may next be used to adjust anterior/posterior adjustment member 104 (not visible) and thus move coupler 106, rotationally moveable arm 128, swing arm 126 and light emitting member 120 to direct plane of light 122 approximately along the midline of the medial side M of the tibia T. As seen when comparing FIGS. 2F and 2G, as positioning device 110 is adjusted, cutting guide's 112 orientation relative to the tibia is also adjusted. In one embodiment, the anterior/posterior orientation may be locked in place via a second locking member. However, this second locking is optional and is not included in the embodiment shown in the figures.

Figure 2H:
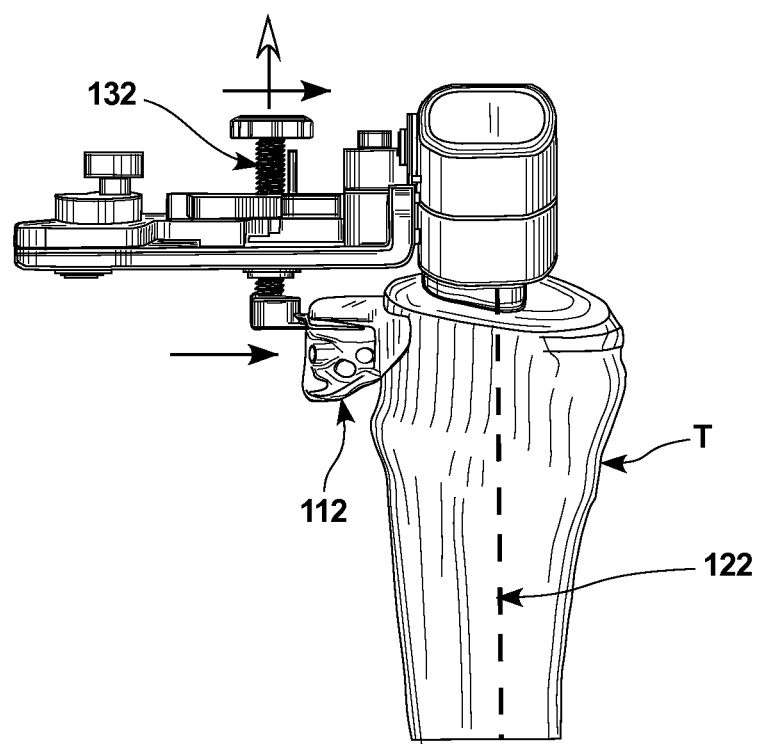

Referring now to FIG. 2H, once varus/valgus and anterior/posterior adjustments have been made, tibial bone resection level adjustment member 132 may turned to move cutting guide 112 up or down relative to the tibia T (hollow-tipped arrow shows upward movement). This upward or downward adjustment may be made by the physician, depending on a desired location of the cutting guide relative to the tibia T. Adjustment member 132 may then be slid along slot 108 (not visible) to move cutting guide 112 into contact with the tibia T (solid-tipped arrows show horizontal movement).

Figure 2I:
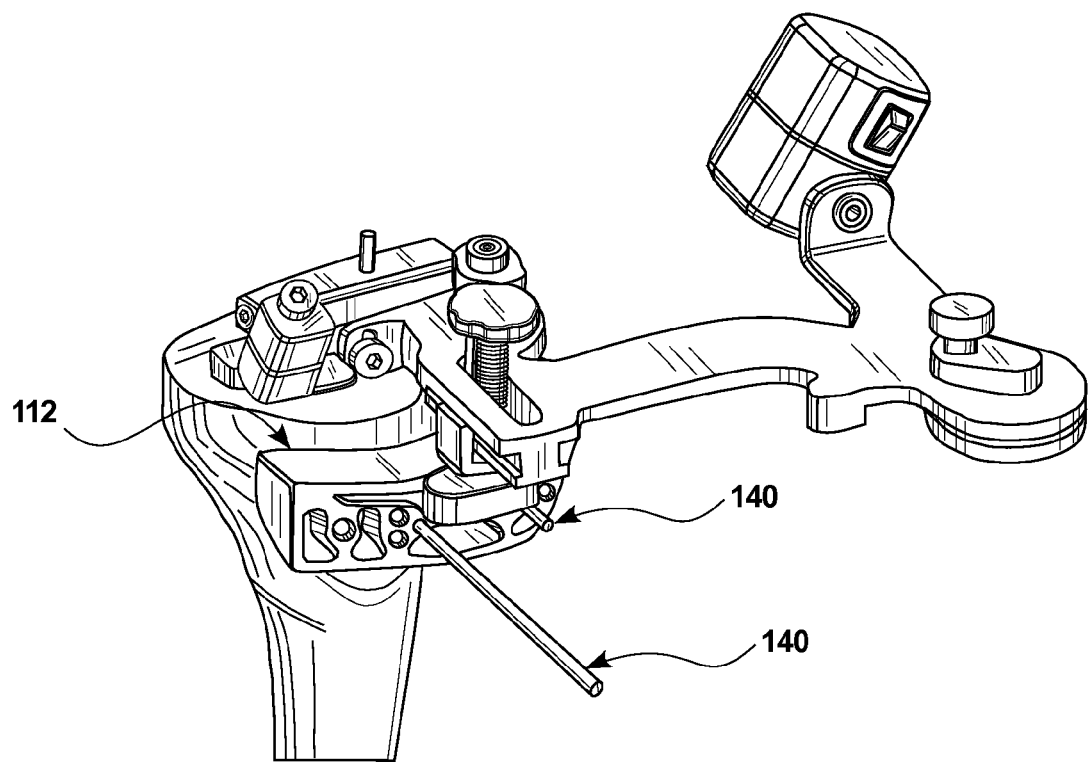
Figure 2J:
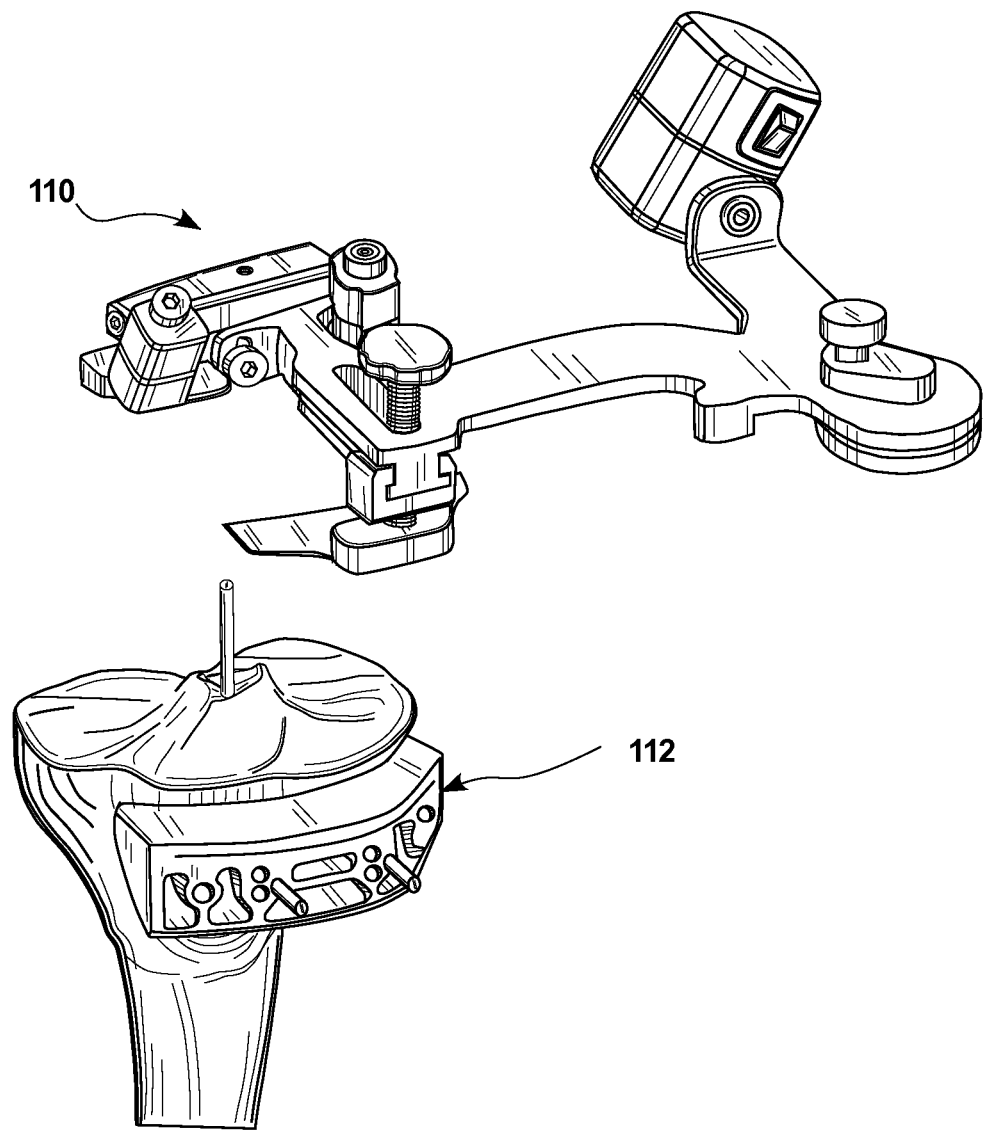

Once cutting guide 112 is in contact with the tibia T, it may be attached to the tibia T using one or more bone attachment pins 140 (or "rods"), as shown in FIG. 2I. Finally, as shown in FIG. 2J, positioning device 110 may be removed, leaving behind cutting guide 112, which the physician may then use to guide a saw blade to cut off a slice of bone from the proximal end of the tibia T. Once the tibial bone cut is made, cutting guide 112 is removed and the rest of the TKA or other knee surgery procedure is performed. As mentioned above, in alternative embodiments, positioning device 110 may be used to mark or otherwise guide a tibial bone cut, thus removing the need for cutting guide 112. In either case, positioning device 110 helps position tibial bone cuts to enhance ligament balancing during a TKA or other knee surgery procedure, and to assure proper alignment of the tibia to the femur.

Figure 3A:
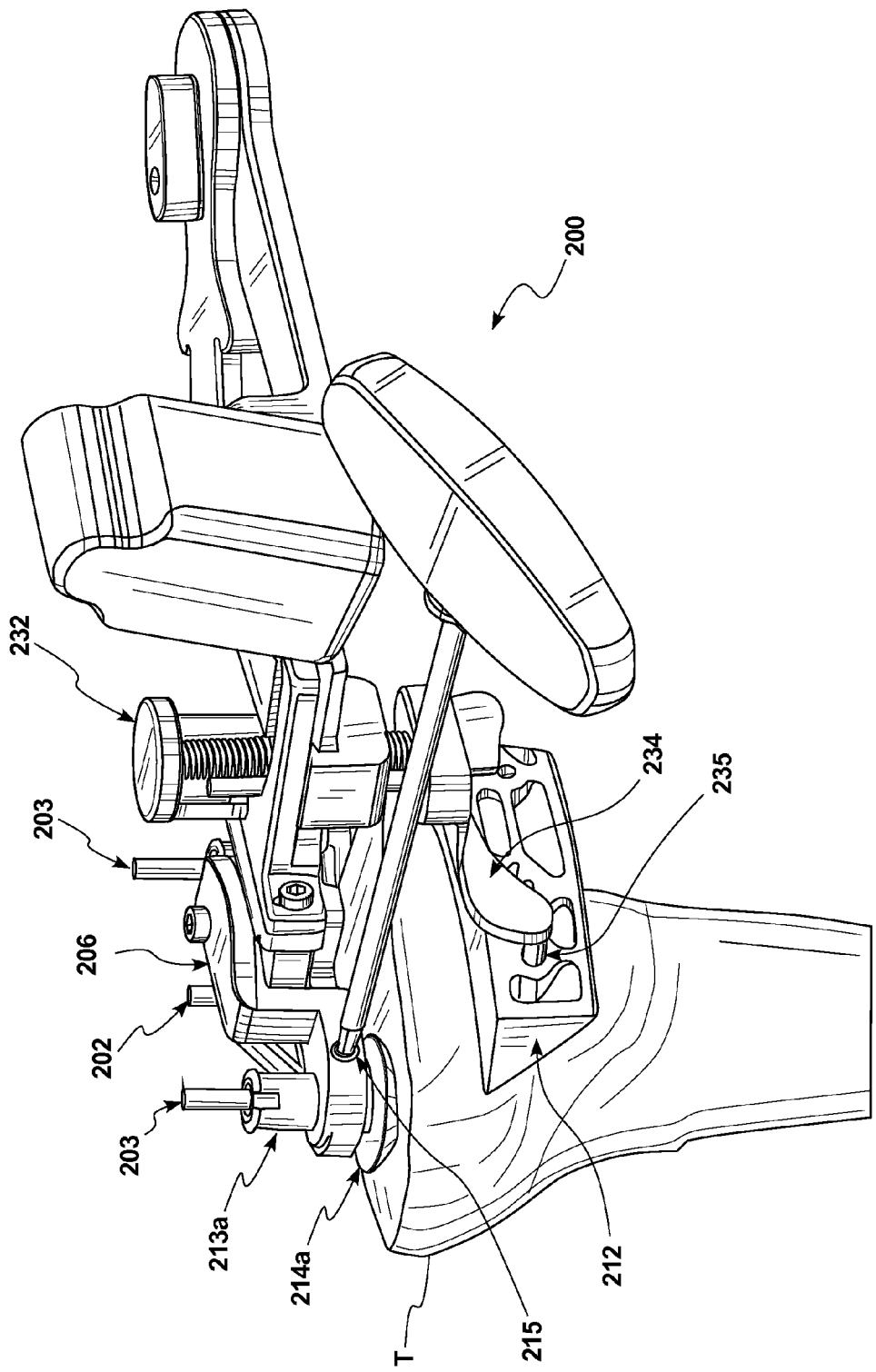
FIG. 3A is a perspective view of a bone cut positioning system coupled with a proximal end of a tibia, according to an alternative embodiment.
Figure 3B:
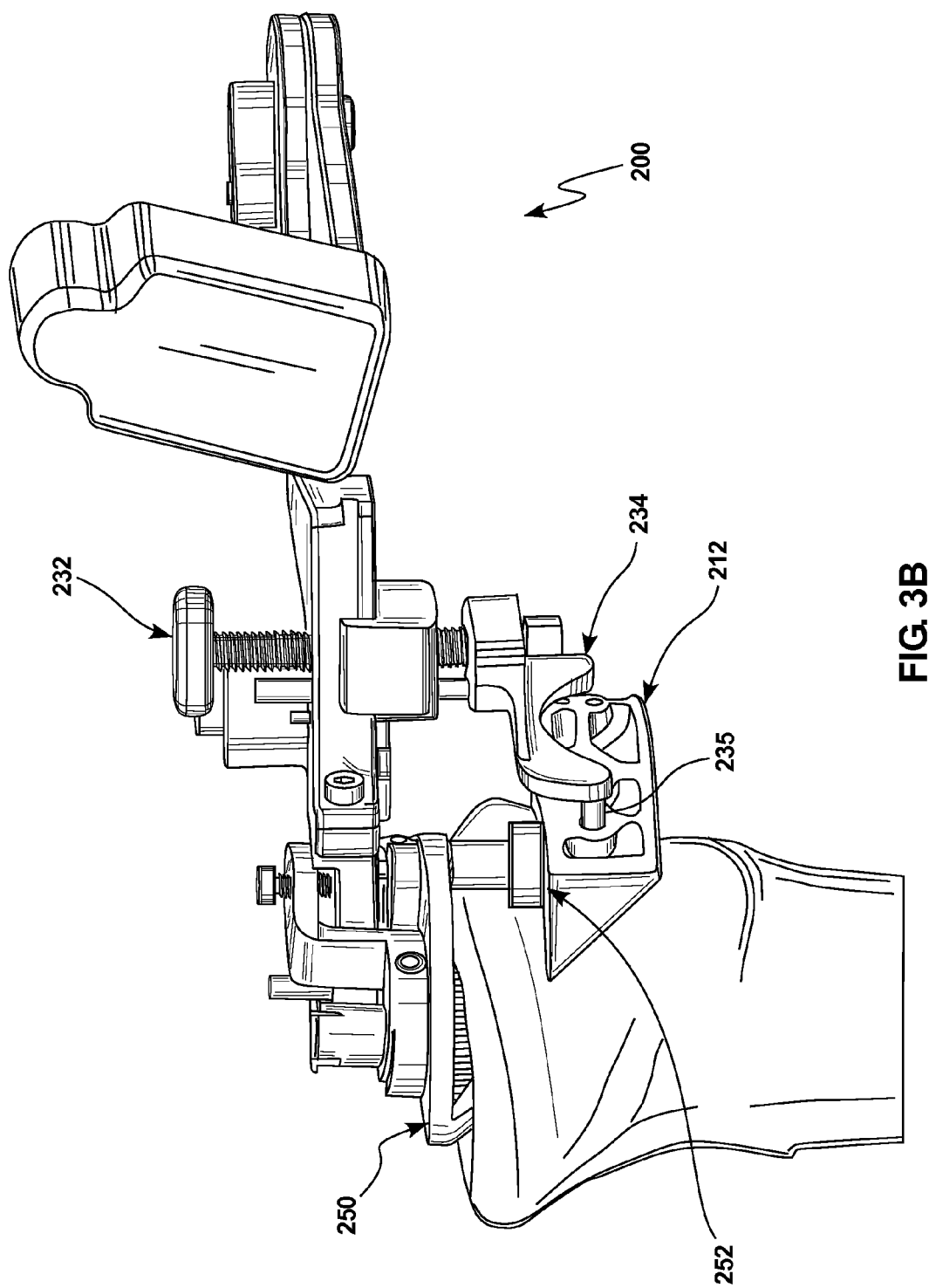
FIGS. 3B and 3C are perspective and posterior views, respectively, of the positioning system of FIG. 3A with the addition of an optional stylus.
Figure 3C:
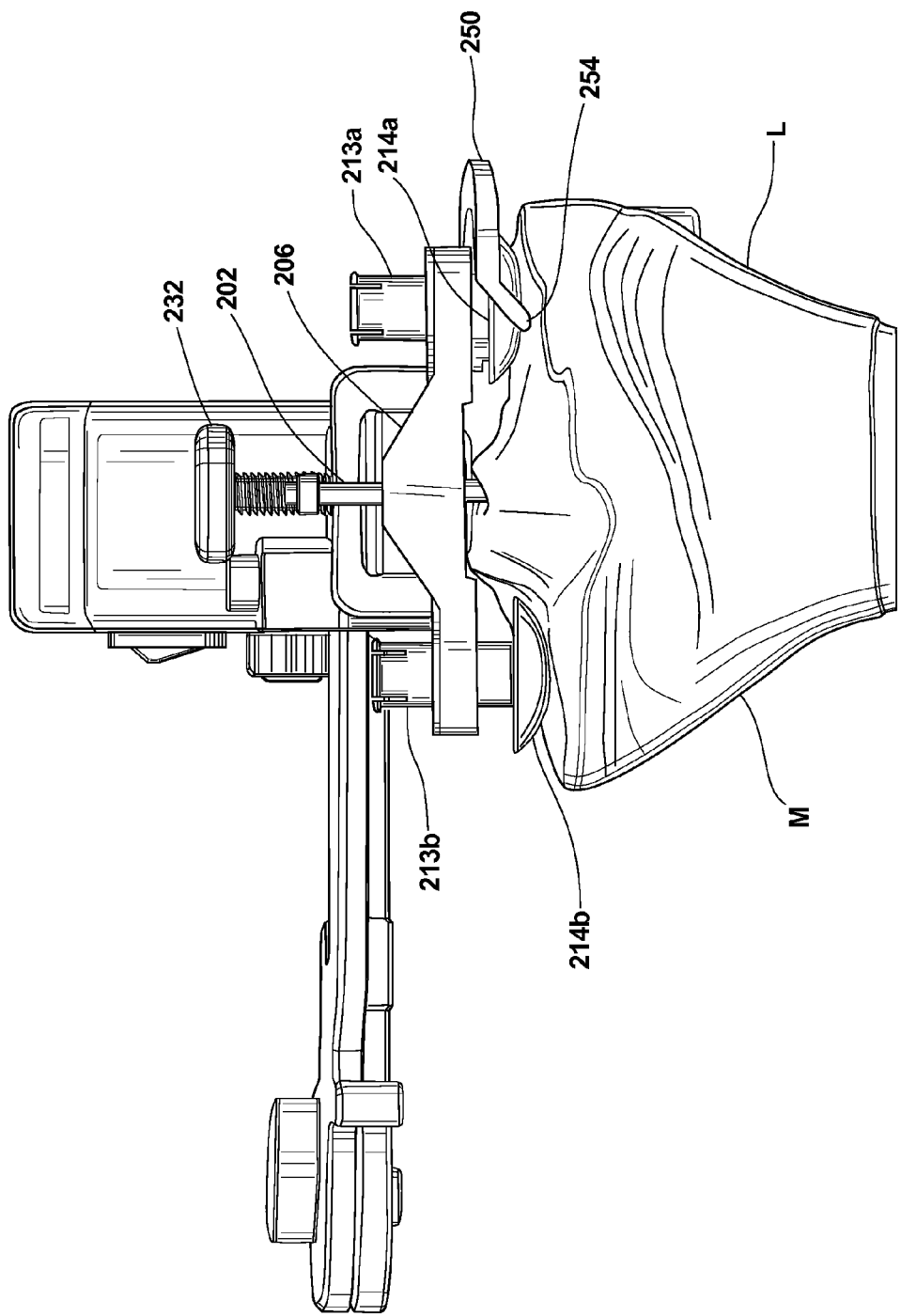

Referring now to FIGS. 3A-3C, another embodiment of a system 200 for positioning a tibial bone cut is shown. Many of the features of system 200 are the same or similar to those described above in reference to FIGS. 1A-1D, and thus those features will not be described here again. In this embodiment, as best seen the posterior view of FIG. 3C, an tibial attachment member 213 includes a lateral attachment member 213a with a lateral footpad 214b and a medial attachment member 213b with a medial footpad 214b. Attachment members 213a, 213b are attached to a tibia T via two reference pins 203, and a coupler 206 is attached to attachment members 213a, 213b. As shown in FIG. 3A, in some embodiments, attachment members 213a, 213b may be locked to coupler 206 using a lock screw 215 or other locking mechanism. As also shown in FIGS. 3A and 3C, coupler may in some embodiments also be attached to the tibia T via another reference pin 202.

System 200 includes an alternative cutting guide holder 234, which includes two rods 235 on which cutting guide 212 rests during adjustments of system 200 to select a desired location for cutting guide 212. As in the previously described embodiment, holder 234 is attached to a bone cut resection level adjustment member 232 configured to move holder 234 up and/or down to select a desired resection level. Adjustment member 232 can also move back and forth through a slot on the rotationally moveable arm, as previously described, to bring cutting guide 212 into or out of contact with the tibia T.

With reference to FIGS. 3B and 3C, in some embodiments, system 200 may include a stylus 250 for determining a bone cut resection level. Stylus 250 is coupled with tibial attachment member 213 and/or coupler 206, according to various embodiments. As seen in FIG. 3C, stylus 250 contacts one of the articular surfaces of the tibia via a tibial contact 254. In the embodiment shown, the lateral articular surface is contacted. As seen in FIG. 3B, stylus 250 wraps around the tibia T and extends to a resection level bumper 252, against which cutting guide 212 may be adjusted to select a desired bone resection level. In this embodiment, wherein tibial contact 254 contacts the lateral articular surface of the tibia T, the contact point of bumper 252 may be between about 8 mm and about 11 mm below the lateral articular surface, and in some embodiments between about 9 mm and about 10 mm below the lateral articular surface. If stylus 250 is instead coupled with a medial articular surface, bumper 252 will likely extend to a different level below the medial articular surface. Generally, stylus 250 is used to help select a desired tibial resection level at which to place cutting guide 212 by adjusting adjustment member 232.

Figure 3D:
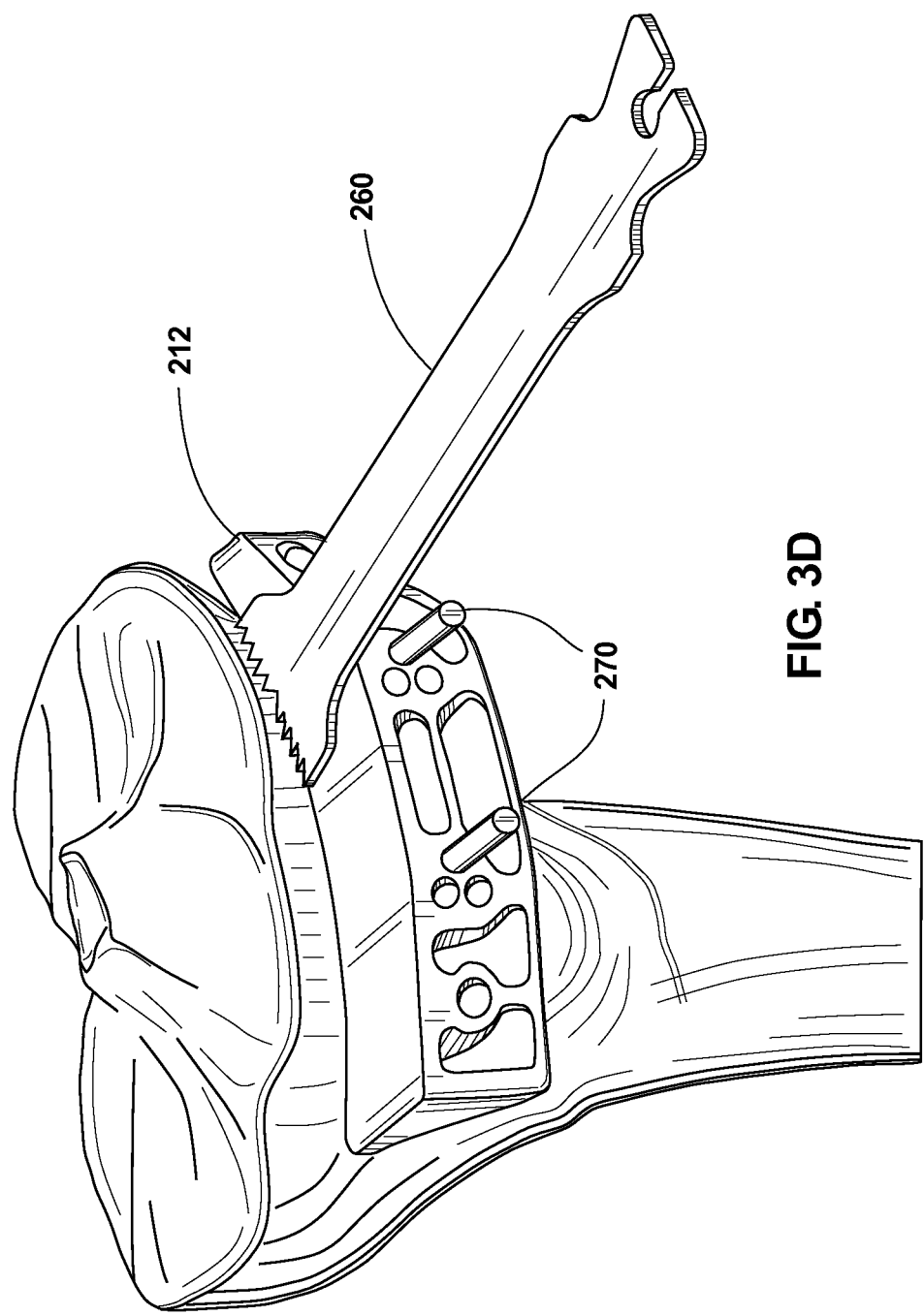
FIG. 3D is a perspective view of a tibia with attached cutting guide and tibial bone saw blade in place after positioning of the cutting guide using the positioning system of FIGS. 3A-3C.

Referring now to FIG. 3D, tibial cutting guide 212 is shown attached to the tibia T via two attachment rods 270 (or "pins"). In alternative embodiments, only one rod 270, more than two rods 270, or any suitable alternative fasteners may be used to attach cutting guide 212 to the tibia T. After cutting guide 212 is attached, a tibial bone saw blade 260 is then used to make the bone cut (or multiple cuts) on the proximal tibia T. Blade 260 is attached to a bone saw (not shown) to make the cut. Once the tibial bone cut is made, cutting guide 212 is removed and the remainder of the TKA or other knee arthroplasty procedure is performed.

Broadly, this writing has disclosed at least the following. A method for positioning a bone cutting guide on a tibia may involve coupling a cutting guide positioning apparatus with a tibia, adjusting the positioning apparatus in a varus/valgus orientation, adjusting the positioning apparatus in an anterior/posterior orientation, adjusting the positioning apparatus up or down to select a tibial bone resection level, and contacting a cutting guide with the tibia, using the adjusted positioning apparatus.

This writing has as well disclosed a device for positioning a bone cut comprising a positioning apparatus to position the device in a varus/valgus orientation, an anterior/posterior orientation, an up or down position. This device may further comprise a light to assist in using said positioning apparatus.

As short summaries, this writing has disclosed at least the following broad concepts.

Concept 1. A device for positioning a bone cut on a tibia, the device comprising:
- a tibial attachment member;
- a coupler moveably attached to the tibial attachment member;
- a rotationally moveable arm rotationally attached to the coupler;
- a swing arm coupled with the rotationally moveable arm via an axle such that a free end of the swing arm swings from an anterior position to a side position;
- a light emitting member coupled with the swing arm at or near the free end for emitting light along the tibia;
- a varus/valgus adjustment member for adjusting the rotationally moveable arm to direct the emitted light approximately along a midline of an anterior surface of the tibia;
- an anterior/posterior adjustment member for adjusting the coupler in an anterior/posterior orientation relative to the tibial attachment member to direct the emitted light approximately along a midline of a side of the tibia; and
- a tibial bone resection level adjustment member for selecting a level for resecting the tibia.

Concept 2. A device as in concept 1, wherein the tibial attachment member comprises:
- at least one foot pad for contacting an articular surface of an uncut tibia; and
- at least one hole for passing the attachment member over a reference pin attached to the tibia.

Concept 3. A device as in concept 2, wherein tibial attachment member comprises:
- a medial articular surface footpad having a first hole; and
- a lateral articular surface footpad having a second hole.

Concept 4. A device as in concept 1, wherein the light emitting member emits light in a linear or planar configuration.

Concept 5. A device as in concept 1, wherein the side of the tibia is the medial side, and wherein the swing arm rotates between a first position in which the light shines along the anterior surface of the tibia and a second position in which the light shines along the medial side of the tibia.

Concept 6. A device as in concept 1, further comprising a tibial cutting guide holder, wherein adjustments of the adjustment members adjust a position of the cutting guide holder.

Concept 7. A device as in concept 1, further comprising a stylus coupled with the tibial attachment member and configured to extend from an upper surface of the tibia to a location anterior to and below the upper surface, wherein the tibial bone resection level adjustment member is adjustable to contact the tibial cutting guide with the stylus at the location.

Concept 8. A system for positioning a tibial cutting guide on a tibia, the system comprising:
- a tibial cutting guide; and
- a cutting guide positioning device comprising:
  - a tibial attachment member;
  - a coupler moveably attached to the tibial attachment member;
  - a rotationally moveable arm rotationally attached to the coupler;
  - a swing arm coupled with the rotationally moveable arm via an axle such that a free end of the swing arm swings from an anterior position to a side position;
  - a light emitting member coupled with the swing arm at or near the free end for emitting light along the tibia;
  - a varus/valgus adjustment member for adjusting the rotationally moveable arm to direct the emitted light approximately along a midline of an anterior surface of the tibia;
  - an anterior/posterior adjustment member for adjusting the coupler in an anterior/posterior orientation relative to the tibial attachment member to direct the emitted light approximately along a midline of a side of the tibia;
  - a tibial bone resection level adjustment member for selecting a level for resecting the tibia; and
  - a tibial cutting guide holder, wherein adjustments of the adjustment members adjust a position of the cutting guide holder.

Concept 9. A system as in concept 8, wherein the tibial cutting guide holder is moveable relative to the rotationally moveable arm to move the tibial cutting guide into contact with the tibia.

Concept 10. A system as in concept 8, further comprising at least one reference pin for removably attaching the tibial attachment member of the guide positioning device to the tibia.

Concept 11. A system as in concept 8, further comprising at least one cutting guide fastener for attaching the tibial cutting guide to the tibia.

Concept 12. A system as in concept 8, wherein the light emitting member emits light in a linear or planar configuration that may be directed along the tibia.

Concept 13. A system as in concept 8, wherein the side of the tibia is the medial side, and wherein the swing arm rotates between a first position in which the light shines along the anterior surface of the tibia and a second position in which the light shines along the medial side of the tibia.

Concept 14. A system as in concept 8, further comprising a stylus coupled with the tibial attachment member and configured to extend from an upper surface of the tibia to a location anterior to and below the upper surface, wherein the tibial bone resection level adjustment member is adjustable to contact the tibial cutting guide with the stylus at the location.

Concept 15. A method for positioning a bone cutting guide on a tibia, the method comprising:
- coupling a cutting guide positioning apparatus with a tibia;
- adjusting the positioning apparatus in a varus/valgus orientation;
- adjusting the positioning apparatus in an anterior/posterior orientation;
- adjusting the positioning apparatus up or down to select a tibial bone resection level; and
- contacting a cutting guide with the tibia, using the adjusted positioning apparatus.

Concept 16. A method as in concept 15, further comprising emitting light in a linear configuration from the cutting guide positioning device, wherein adjusting the apparatus in the varus/valgus orientation comprises moving the light to shine along approximately a midline of an anterior surface of the tibia, and wherein adjusting the apparatus in the anterior/posterior orientation comprises moving the light to shine along approximately a midline of a side of the tibia.

Concept 17. A method as in concept 16, wherein the side of the tibia comprises a medial side.

Concept 18. A method as in concept 16, further comprising swinging a swing arm of the cutting guide positioning apparatus approximately 90 degrees between the steps of adjusting in the varus/valgus orientation and adjusting in the anterior/posterior orientation.

Concept 19. A method as in concept 18, further comprising locking in the varus/valgus orientation before swinging the swing arm.

Concept 20. A method as in concept 15, wherein the cutting guide is removably coupled with the guide positioning apparatus during the adjusting steps.

Concept 21. A method as in concept 15, further comprising attaching the cutting guide to the tibia.

Concept 22. A method as in concept 21, further comprising:
 removing the positioning apparatus from the tibia and the cutting guide; and
 making at least one cut on the tibia guided by the cutting guide.

Concept 23. A method as in concept 21, wherein adjusting the positioning apparatus up or down to select a tibial bone resection level comprises moving a resection level adjustment member up or down to contact a stylus touching an upper surface of the tibia and extending to a location anterior to and below the upper surface.

Concept 24. A method as in concept 23, wherein the location is between about 8 mm and about 11 mm below the upper surface, and wherein the upper surface is a lateral articular surface of the tibia.

Concept 25. A method as in concept 21, wherein coupling the cutting guide positioning apparatus with the tibia comprises advancing the at least one hole in the apparatus over at least one reference pin attached to the tibia.

Concept 26. A method as in concept 25, wherein two foot pads of the positioning device are advanced over two reference pins to contact the medial and lateral articular surfaces of the tibia.

Concept 27. A method for positioning a bone cutting guide on a tibia, the method comprising:
 coupling a cutting guide positioning apparatus with a tibia, wherein the positioning apparatus is coupled with a tibial cutting guide;
 emitting a light from the positioning apparatus;
 adjusting the positioning apparatus in a varus/valgus orientation to shine the light approximately along a midline of an anterior surface of the tibia;
 swinging a swing arm of the positioning apparatus approximately 90 degrees to shine the light along a side of the tibia;
 adjusting the positioning apparatus in an anterior/posterior orientation to shine the light approximately along a midline of the side of the tibia;
 adjusting the positioning apparatus up or down to select a tibial bone resection level; and
 attaching the tibial cutting guide to the tibia, using the adjusted positioning apparatus.

Concept 28. A method as in concept 27, further comprising:
 removing the positioning apparatus from the tibia and the cutting guide; and
 making at least one cut on the tibia guided by the cutting guide.

Concept 29. A method as in concept 27, wherein the side of the tibia comprises a medial side.

Concept 30. A device for positioning a bone cut on a tibia, the device comprising:
 a tibial attachment member;
 a first adjustment member for adjusting the device in a varus/valgus orientation;
 a second adjustment member for adjusting the device in an anterior/posterior orientation; and
 a third adjustment member for selecting a level of resecting the tibia.

Concept 31. A system for positioning a bone cut on a tibia, the device comprising:
 a tibial cutting guide positioning device, comprising:
  a tibial attachment member;
  a first adjustment member for adjusting the device in a varus/valgus orientation;
  a second adjustment member for adjusting the device in an anterior/posterior orientation; and
 a tibial cutting guide removably attached to the positioning device.

Concept 32. A device for positioning a bone cut on a tibia, the device comprising:
 a tibial attachment member;
 a first adjustment member for adjusting the device in a varus/valgus orientation;
 a second adjustment member for adjusting the device in an anterior/posterior orientation;
 a light emitting member coupled with device and configured to emit a light along a surface of the tibia and to move in response to adjustments of the first and second adjustment members; and
 a third adjustment member for selecting a level of resecting the tibia.

Otherwise put, this writing has disclosed a device for positioning a bone cut on a tibia, the device comprising a tibial attachment member, a first adjustment member for adjusting the device in a varus/valgus orientation, a second adjustment member for adjusting the device in an anterior/posterior orientation, and a third adjustment member for selecting a level for resecting the tibia. Further, this writing has disclosed a system for positioning a bone cut on a tibia, the device comprising a tibial cutting guide positioning device, comprising a tibial attachment member, a first adjustment member for adjusting the device in a varus/valgus orientation, a second adjustment member for adjusting the device in an anterior/posterior orientation, and a third adjustment member for selecting a level for resecting the tibia, and a tibial cutting guide removably attached to the positioning device.

In more detail, this writing has disclosed a device for positioning a bone cut on a tibia, the device comprising a tibial attachment member, a first adjustment member for adjusting the device in a varus/valgus orientation, a second adjustment member for adjusting the device in an anterior/posterior orientation, a light emitting member coupled with device and configured to emit a light along a surface of the tibia and to move in response to adjustments of the first and second adjustment members and a third adjustment member for selecting a level for resecting the tibia.

The present technology may be embodied in other specific forms without departing from the essential characteristics thereof. For example, in alternative embodiments method steps may be deleted, added or performed in a different order than that described above. In one embodiment, for example, it may be possible to perform the anterior/posterior adjustment prior to the varus/valgus adjustment. Thus, the embodiments described above as well as alternative embodiments and equivalents are intended to be included within the scope of the present technology, which is set forth in the following claims

The invention claimed is:

1. A device for positioning a bone cut on a tibia, the device comprising:
 a tibial attachment member;
 a coupler moveably attached to the tibial attachment member;
 a rotationally moveable arm rotationally attached to the coupler;
 a swing arm coupled with the rotationally moveable arm via an axle such that a free end of the swing arm is configured to swing from an anterior position, in which the free end faces an anterior surface of the tibia, to a side position, in which the free end faces a side of the tibia;

a light emitting member coupled with the swing arm at or near the free end for emitting light along the tibia, the light emitting member emitting light in a linear or planar configuration;

a varus/valgus adjustment member for adjusting the rotationally moveable arm to direct the emitted light approximately along a midline of the anterior surface of the tibia;

an anterior/posterior adjustment member for adjusting the coupler in an anterior/posterior orientation relative to the tibial attachment member to direct the emitted light approximately along a midline of the side of the tibia; and a tibial bone resection level adjustment member for selecting a level for resecting the tibia.

2. A device as in claim 1, wherein the tibial attachment member comprises:

at least one foot pad for contacting an articular surface of an uncut tibia; and at least one hole for passing the attachment member over a reference pin attached to the tibia.

3. A device as in claim 2, wherein tibial attachment member comprises:

a medial articular surface footpad having a first hole; and a lateral articular surface footpad having a second hole.

4. A device as in claim 1, wherein the side of the tibia is the medial side, and wherein the swing arm is configured to rotate between a first position in which the light shines along the anterior surface of the tibia and a second position in which the light shines along the medial side of the tibia.

5. A device as in claim 1, further comprising a tibial cutting guide holder, wherein adjustments of the adjustment members adjust a position of the cutting guide holder.

6. A device as in claim 1, further comprising a stylus coupled with the tibial attachment member and configured to extend from an upper surface of the tibia to a location anterior to and below the upper surface, wherein the tibial bone resection level adjustment member is adjustable to contact the tibial cutting guide with the stylus at the location.

7. A device as in claim 1, wherein the light emitting member emits light in a linear or planar configuration selected from a group of configurations including:

a beam;

a plane; and a fan.

8. A system for positioning a tibial cutting guide on a tibia, the system comprising:

a tibial cutting guide; and a cutting guide positioning device comprising: a tibial attachment member;

a coupler moveably attached to the tibial attachment member;

a rotationally moveable arm rotationally attached to the coupler;

a swing arm coupled with the rotationally moveable arm via an axle such that a free end of the swing arm is configured to swing from an anterior position, in which the free end faces an anterior surface of the tibia, to a side position, in which the free end faces a side of the tibia;

a light emitting member coupled with the swing arm at or near the free end for emitting light along the tibia, the light emitting member emitting light in a linear or planar configuration;

a varus/valgus adjustment member for adjusting the rotationally moveable arm to direct the emitted light approximately along a midline of the anterior surface of the tibia;

an anterior/posterior adjustment member for adjusting the coupler in an anterior/posterior orientation relative to the tibial attachment member to direct the emitted light approximately along a midline of the side of the tibia; and a tibial bone resection level adjustment member for selecting a level for resecting the tibia; and a tibial cutting guide holder, wherein adjustments of the adjustment members adjust a position of the cutting guide holder.

9. A system as in claim 8, wherein the tibial cutting guide holder is moveable relative to the rotationally moveable arm to move the tibial cutting guide into contact with the tibia.

10. A system as in claim 8, further comprising at least one reference pin for removably attaching the tibial attachment member of the guide positioning device to the tibia.

11. A system as in claim 8, further comprising at least one cutting guide fastener for attaching the tibial cutting guide to the tibia.

12. A system as in claim 8, wherein the side of the tibia is the medial side, and wherein the swing arm is configured to rotate between a first position in which the light shines along the anterior surface of the tibia and a second position in which the light shines along the medial side of the tibia.

13. A system as in claim 8, further comprising a stylus coupled with the tibial attachment member and configured to extend from an upper surface of the tibia to a location anterior to and below the upper surface, wherein the tibial bone resection level adjustment member is adjustable to contact the tibial cutting guide with the stylus at the location.

* * * * *